(12) United States Patent
Bandla et al.

(10) Patent No.: US 7,585,641 B2
(45) Date of Patent: Sep. 8, 2009

(54) IMMUNOASSAY AND METHOD OF USE

(75) Inventors: Murali D. Bandla, Granger, IN (US);
Matthew R. Chambers, Edwardsburg, MI (US); Chester L. Sutula, Elkhart, IN (US)

(73) Assignee: Agdia, Inc., Elkhart, IN (US)

( * ) Notice: Subject to any disclaimer, the term of this patent is extended or adjusted under 35 U.S.C. 154(b) by 1326 days.

(21) Appl. No.: 10/348,078

(22) Filed: Jan. 21, 2003

(65) Prior Publication Data

US 2004/0142398 A1 Jul. 22, 2004

(51) Int. Cl.
*C12N 7/00* (2006.01)
*C12N 7/01* (2006.01)
*C12N 11/14* (2006.01)
*C12N 13/00* (2006.01)
*C12Q 1/06* (2006.01)
*C12Q 1/70* (2006.01)
*G01N 33/53* (2006.01)

(52) U.S. Cl. ............... 435/7.8; 435/4; 435/5; 435/39; 435/173.4; 435/174; 435/176; 435/235.1; 435/239; 435/410; 436/501; 436/523; 436/533

(58) Field of Classification Search ............ 435/4, 435/5, 7.1, 7.2, 7.91, 29, 283.1, 286.1, 287.1, 435/287.2, 288.1; 436/164, 174, 501, 507, 436/518, 519, 523, 527, 536
See application file for complete search history.

(56) References Cited

U.S. PATENT DOCUMENTS

| | | | | |
|---|---|---|---|---|
| 4,871,540 A | * | 10/1989 | Kojima et al. | 424/750 |
| 5,043,263 A | * | 8/1991 | Hammond et al. | 435/5 |
| 5,753,517 A | * | 5/1998 | Brooks et al. | 436/514 |

* cited by examiner

*Primary Examiner*—Robert B Mondesi
*Assistant Examiner*—JaNa Hines
(74) *Attorney, Agent, or Firm*—Ian C. McLeod

(57) ABSTRACT

A method for performing an immunoassay is described. The method is particularly useful for detecting extracellular polysaccharide (EPS) and/or lipopolysaccharide (LPS) producing microorganisms. The method is particularly useful for detecting microorganisms which produce extracellular polysaccharides (EPS) also known as exocellular polysaccharides, capsule, and/or lipopolysaccharides (LPS). In a preferred method for detecting microorganisms which produce EPS, LPS, or both, the EPS and/or LPS is extracted from a sample with cetyltrimethylammonium bromide (CTAB) to produce molecular aggregates which are then preferentially bound to colored polystyrene latex particles over other components in the sample, and the bound EPS and/or LPS detected using a lateral flow immunoassay apparatus which has immobilized thereon antibodies specific for the EPS and/or LPS. The method can also be used to detect particular viruses, for example viruses of the potyviridae or tobamoviridae group.

19 Claims, 22 Drawing Sheets

1 2 3 4

IMMUNOASSAY AND METHOD OF USE

CROSS-REFERENCE TO RELATED APPLICATION

Not applicable.

STATEMENT REGARDING FEDERALLY SPONSORED RESEARCH OR DEVELOPMENT

Not applicable.

REFERENCE TO A "COMPUTER LISTING APPENDIX SUBMITTED ON A COMPACT DISC"

Not Applicable.

BACKGROUND OF THE INVENTION (1) Field of the Invention

The present invention relates to a method for performing an immunoassay for detecting an analyte which uses colored polystyrene latex particles for detecting the analyte. The method is particularly useful for detecting microorganisms which produce extracellular polysaccharides (EPS) also known as exocellular polysaccharides, capsule, and/or lipopolysaccharides (LPS). In a preferred method for detecting microorganisms which produce EPS, LPS, or both, the EPS and/or LPS is extracted from a sample with cetyltrimethylammonium bromide (CTAB) to produce molecular aggregates which are then preferentially bound to colored polystyrene latex particles over other components in the sample, and the bound EPS and/or LPS detected using a lateral flow immunoassay apparatus which has immobilized thereon antibodies specific for the EPS and/or LPS. The method can also be used to detect particular viruses, for example viruses of the potyviridae or tobamoviridae group.

(2) Description of Related Art

Bacterial plant pathogens cause many important diseases of field and orchard crops and produce damages worth many millions of dollars (Goto, In: Fundamentals of Bacterial Plant Pathology, Academic Press, New York, N.Y. (1990)). Some of these pathogens have been present in U.S. for many years. Others have not been detected in this country; however, their introduction may produce quarantine actions and cause serious economic loss. During the month of August, 2002 USDA-APHIS released a list of potential pathogens which could be used for agricultural bioterrorism. Among the nine pathogens listed, four are bacterial plant pathogens such as *Ralstonia solanacearum* (Rs) race 3.

Traditional diagnosis of bacterial plant pathogens involved isolating bacteria from an infected sample using selective media and studying its morphological, nutritional, and biochemical characteristics (Schaad et al., In: Laboratory Guide for Identification of Plant Pathogenic Bacteria, $3^{rd}$ Edition. APS Press, St. Paul, Minn. (2000)). Several analytical procedures based on nutritional (MICROLOG Microbial Identification System, Biolog Inc., Hayward, Calif.) and fatty acid analysis are commercially available. However, these procedures require trained personnel and in many cases, the data turn-around time is considerable.

New molecular biology techniques such as polymerase chain reaction (PCR) and real-time PCR offer specific and sensitive diagnosis. However these procedures are expensive, require specialized equipment, lengthy sample processing protocols, and skilled personnel. Real-time PCR with molecular beacons (Tyagi and Kramer, Nature Biotecnol. 14: 303-308 (1996)) and nucleic acid sequence-based amplification (NASBA) (Compton, Nature. 350: 91-92 (1991)) are some of the newest DNA-based assays which are rapid and sensitive. While such molecular diagnostics are effective, in practice they require a high level of expertise, demanding sample extraction methodologies, and a generous diagnostic budget. An enrichment PCR assay, called "BIO-PCR", shows greater sensitivity than direct PCR (Schaad et al., Plant Dis. 83: 1095-1100 (1999)) when used to detect pathogen from plant samples. However, the principle of sample enrichment by culturing in a media also enhances the sensitivity of serological tests. For example, Hoszowski et al., Int. J. Food Microbiol. 28: 341-350 (1996) were able to detect as few as five colony-forming units (pre-enrichment number) of *Salmonella* from 100 mL of chicken carcass rinsing with a filtration, enrichment, and colony blot immunoassay technique. A rational approach may be testing a higher volume of samples using a rapid inexpensive diagnostic test and confirming positives with PCR by sending the sample to a diagnostic lab.

Serological tests such as traditional agar double-diffusion assays and more recently, enzyme linked immunosorbent assay (ELISA), immunoblots, immunofluorescence (IF), and lateral flow immunoassays (LFA) have also been used extensively for diagnosis of plant bacterial pathogens (Alvarez, In: Plant Pathogenic Bacteria, 3rd Edition. Schaad et al., Eds. APS Press, St. Paul, Minn. (2000), pp. 338-342). In general, these tests have been of limited use because of their lack of specificity and sensitivity and cross-reactivity to other bacterial species. Older serological tests utilizing polyclonal antibodies made against bacterial proteins are of limited utility due to their cross reactivity (Robinson-Smith et al., Food and Agricultural Immunol. 7: 67-79(1995)) and specificity (Hampton, In: Serological Methods for Detection and Identification of Viral and Bacterial Plant Pathogens, a Laboratory Manual. APS Press, St. Paul, Minn. (1990)). The invention of monoclonal antibody technology by Kohler and Milstein in 1975 stimulated rapid progress in serological techniques. Hybridoma technology has been used to generate and characterize monoclonal antibodies (MAbs) specific for several species of bacterial plant pathogens (Alvarez et al., Phytopathol. 75: 722-728 (1985); Alvarez et al., Phytopathol. 81: 857-865 (1991); Alvarez et al., In: Bacterial Wilt International Conf., Kaohsiung, Taiwan, ACIAR Proc. No. 45. (1992), pp. 62-69; Alvarez et al., Plant Pathology 45: 358-366 (1996); Alvarez et al., In: Seed Health Testing: Progress Towards the 21st Century. Hutchins and Reeves, Eds. CAB International, Wallingford, United Kingdom (1998), pp. 175-183; Alvarez et al., In: Proc. $3^{rd}$. International Seed Testing Association, Seed Health Symposium, Iowa State University, Ames (1999), pp. 110-114; Jordan, In: Molecular Methods in Plant Pathology, Singh, Ed., Lewis Publishers, Inc., Boca Raton, Fla. (1995), pp. 395-412 (1995); Hampton et al., Serological Methods for Detection and Identification of Viral and Bacterial Plant Pathogens, a Laboratory Manual. APS Press, St. Paul, Minn. (1990); Torrance, Euro. J. Plant Pathol. 101: 351-363 (1995); Wong, LETT. APPL. M. 10: 241-244 (1990). Thus, by using hybridoma technology, monoclonal antibodies have been produced which can differentiate bacterial strains, races, and biovars within the same genus (Alvarez and Bennedict, In: Methods in Phytobacteriology. Klement et al. Eds. Akademiai Kiado Budapest (1990), pp. 180-185; Goto, In: Fundamentals of Bacterial Plant Pathology, Academic Press, New York (1990)). Thus, immunodiagnostic techniques which use monoclonal antibodies (MAbs) are now used for detection of pathogenic bacteria both from seed (Alvarez and Kaneshiro, In: Proc. 3$^{rd}$ Intl. Seed Testing Assoc., Seed Health Symp., Iowa State University, Ames, Iowa (1999), pp. 93-97; Alvarez et al., In: Seed Health Testing: Progress Towards the 21$^{st}$ Century, Hutchins and Reeves, Eds., CAB International, Wallingford, UK (1997), pp. 175-183)) and other plant materials (Baer and Gudmestad, Phytopathol. 83: 157-163 (1993); Gitaitis et al., Plant Dis. 75: 834-838 (1991); McLaughlin and Chen, In: Serological Methods for Detection and Identification of Viral and Bacterial Plant Pathogens, a Laboratory Manual. Hampton et al., Eds., APS Press, St. Paul, Minn. (1990), pp. 197-205.

Lateral flow immunostrip assays have several advantages over other currently available formats such as simple to use, portable, inexpensive, stable, and have longer shelf-life. There is extensive art in the field of lateral flow immunostrip technology which is exemplified by the following patents: U.S. Pat. No. 6,391,652 B1 to Okada et al.; U.S. Pat. No. 6,368,875 to Geisberg; U.S. Pat. No. 6,352,862 B1 to Davis et al.; U.S. Pat. No. 6,342,396 B1 to Perrin et al.; U.S. Pat. No. 6,228,660 B1 to May et al.; U.S. Pat. No. 6,180,417 B1 to Hajizadeh et al.; U.S. Pat. No. 5,989,921 to Charlton et al.; U.S. Pat. No. 5,965,458 to Kouvonen et al.; U.S. Pat. No. 5,877,028 to Chandler et al.; U.S. Pat. No. 5,827,749 to Akers, Jr.; U.S. Pat. No. 5,814,407 to Richard et al.; U.S. Pat. No. 5,766,961 to Pawlak et al.; U.S. Pat. No. 5,770,460 to Pawlak et al.; U.S. Pat. No. 5,741,662 to Madsen et al.; U.S. Pat. No. 5,716,778 to Weng et al.; U.S. Pat. No. 5,712,172 to Huang et al.; U.S. Pat. No. 5,712,170 to Kouvonen et al.; U.S. Pat. No. 5,695,928 to Stewart; U.S. Pat. No. 5,686,315 Pronovost et al.; U.S. Pat. No. 5,654,162 to Guire et al.; U.S. Pat. No. 5,620,845 to Gould et al.; U.S. Pat. No. 5,591,645 to Rosenstein; U.S. Pat. No. 5,498,551 to de Jaeger et al.; U.S. Pat. No. 5,489,537 to Van Aken; U.S. Pat. No. 5,437,983 to Watts et al.; U.S. Pat. No. 5,424,193 to Pronovost et al.; U.S. Pat. No. 5,415,994 to Imrich et al.; U.S. Pat. No. 5,266,497 to Imai et al.; U.S. Pat. No. 5,252,459 to Tarcha et al.; U.S. Pat. No. Re. 34,405 to Gould et al.; U.S. Pat. No. 5,238,652 to Sun et al.; U.S. Pat. No. 5,225,322 to Wolf; U.S. Pat. No. 5,212,061 to Snyder et al.; U.S. Pat. No. 5,096,837 Fan et al.; U.S. Pat. No. 5,075,078 to Osikowicz et al.; U.S. Pat. No. 5,030,561 to Mapes et al.; U.S. Pat. No. 5,028,535 to Buechler et al.; U.S. Pat. No. 4,954,452 to Yost et al.; U.S. Pat. No. 4,952,520 to Okusa et al.; U.S. Pat. No. 4,943,522 to Eisinger et al.; U.S. Pat. No. 4,920,046 to McFarland et al.; U.S. Pat. No. 4,861,711 to Friesen et al.; U.S. Pat. No. 4,855,240 to Rosenstein et al.; U.S. Pat. No. 4,837,168 to de Jaeger et al.; U.S. Pat. No. 4,703,017 to Campbell et al.; U.S. Pat. No. 4,663,277 to Wang; U.S. Pat. No. 4,639,425 to Baier; U.S. Pat. No. 4,435,504 to Zuk et al.; U.S. Pat. No. 4,415,700 to Batz et al.; U.S. Pat. No. 4,376,110 to David et al.; U.S. Pat. No. 4,313,734 to Leuvering; U.S. Pat. No. 4,187,075 to Nöller; U.S. Pat. No. 4,168,146 to Grubb et al.; and European Patent Application No. EP0810436 to Davis et al.

It has been recognized that a preferred assay for detecting microorganisms and viruses, in particular, microorganisms which produce extracellular polysaccharides (EPS) and/or lipopolysaccharides (LPS), would be portable and simple to use such that no special training or equipment would be required to perform the assay. However, in spite of recent improvements in diagnostic methods for detecting microorganisms and viruses, a rapid, field-based diagnostic method for detection of EPS and/or LPS produced by microorganisms as an indicator of infection by the microorganism is still lacking, in particular, an assay for detecting a microorganism which does not kill the microorganism. Such an assay would be particularly useful for detecting microorganisms which infect plants and microorganisms which cause systemic infections in animals or humans.

SUMMARY OF THE INVENTION

The present invention provides a method for performing an immunoassay for detecting an analyte which uses colored polystyrene latex particles for detecting the analyte. The method is particularly useful for detecting microorganisms which produce extracellular polysaccharides (EPS) also known as exocellular polysaccharides, capsule, and/or lipopolysaccharides (LPS). In a preferred method for detecting microorganisms which produce EPS, LPS, or both, the EPS and/or LPS is extracted from a sample with cetyltrimethylammonium bromide (CTAB) to produce molecular aggregates which are then preferentially bound to colored polystyrene latex particles over other components in the sample, and the bound EPS and/or LPS detected using a lateral flow immunoassay apparatus which has immobilized thereon antibodies specific for the EPS and/or LPS. The method can also be used to detect particular viruses, for example viruses of the potyviridae or tobamoviridae group. Particular embodiments of the present invention are set forth below.

In one embodiment of the present invention, the present invention provides a method for determining whether a material contains a microorganism by detecting the presence of an extracellular polysaccharide (EPS), a lipopolysaccharide (LPS), or both, produced by the microorganism, which comprises (a) providing a detection apparatus which includes mounted on a support member an elongated membrane having a first end and a second end wherein in lateral contact with the first end of the membrane is a sample pad for receiving a liquid sample and in lateral contact with the second end of the membrane is a wicking pad which allows the liquid sample to flow through the membrane from the sample pad to the wicking pad and wherein the membrane further comprises at least one detection zone laterally spaced from the sample pad in which is immobilized an antibody which is specific for the EPS or LPS of the microorganism; (b) mixing the material with an extraction solution to produce a mixture including the EPS, LPS, or both; (c) mixing an aliquot of the mixture in step (b) with particles, preferably colored, at room temperature for a time sufficient to bind the EPS, LPS, or both, to the particles without substantial binding of other components of the mixture; (d) mixing a particle blocking solution including a blocking agent with the mixture in step (c) at room temperature for a time sufficient to block sites on the particles not bound to the EPS, LPS, or both; and (e) applying the mixture in step (d) to the sample pad in the detection apparatus at room temperature, wherein presence of the microorganism in the material is indicated by a visible signal produced by binding of the EPS or LPS bound to the particles by the antibody specific for the EPS or LPS immobilized in the detection zone.

In a preferred embodiment of the above method, the membrane further includes a reference zone laterally spaced between the detection zone and the wicking pad in which is immobilized therein a control antibody and the particle blocking solution further includes particles which have bound thereon an antigen which binds the control antibody.

In a preferred embodiment of the above method, the particles are polystyrene latex particles which preferably have a diameter from about 0.06 μm to 1.0 μm, most preferably, a diameter of about 0.77 μm.

In a further embodiment of the above method, the extraction solution includes a salt, preferably 2% NaCl, in a buffer such as 2 mM Tris-HCl, pH 9.2.

In one embodiment of the above method, the material is boiled in the extraction solution for a time sufficient to extract the EPS and/or LPS into the extraction solution. However, in a preferred embodiment, the extraction solution includes cetyltrimethylammonium bromide (CTAB) in a high salt buffer wherein the CTAB and the high salt selectively extracts the EPS, LPS, or both, from the microorganism and material into the extraction solution. Preferably, the CTAB is at a concentration between about 0.25% and 2% and the salt is NaCl at a concentration of about 2% in a buffer such as 2 mM Tris-HCl, pH 9.2.

In a further embodiment of the above method, the particle blocking agent is bovine serum albumin. Preferably, the particle blocking solution includes bovine serum albumin and polysorbate 20 in a buffer and most preferably, the particle blocking solution includes bovine serum albumin, polysorbate 20, and n-dodecyl-N,N-dimethyl glycine in a buffer.

In a further embodiment of the above method, the membrane is a nitrocellulose membrane, preferably a nitrocellulose membrane which has a pore size from about 10 to 20 μm, most preferably, a pore size of about 15 μm. In a further embodiment, the membrane has been treated with a blocking agent, preferably, a blocking agent such as bovine serum albumin.

In a further embodiment of the above method, the sample pad includes a polyester or glass fibers which preferably has been treated with a blocking agent which is preferably selected from the group consisting of bovine serum albumin, non-fat dry milk, and mixtures thereof.

In a further embodiment of the above method, the wicking pad includes a cellulosic material.

In a further embodiment of the above method, the material is a plant material or the material is serum or tissue from an animal or human.

In a further embodiment of the present invention, the present invention provides a method for determining whether an organism is infected with a microorganism by detecting the presence of an extracellular polysaccharide (EPS), a lipopolysaccharide (LPS), or both, produced by the microorganism, which comprises (a) providing a detection apparatus which includes mounted on a support member an elongated membrane having a first end and a second end wherein in lateral contact with the first end of the membrane is a sample pad for receiving a liquid sample and in lateral contact with the second end of the membrane is a wicking pad which allows the liquid sample to flow through the membrane from the sample pad to the wicking pad and wherein the membrane further comprises at least one detection zone laterally spaced from the sample pad in which is immobilized an antibody which is specific for the EPS or LPS of the microorganism; (b) mixing a material from the organism with an extraction solution which includes cetyltrimethylammonium bromide (CTAB) in a high salt buffer at room temperature for a time sufficient to extract the EPS, LPS, or both, from the microorganism and material into the extraction solution; (c) mixing an aliquot of the mixture in step (b) with particles, preferably colored, at room temperature for a time sufficient to preferentially bind the EPS, LPS, or both, to the particles without substantial binding of other components of the mixture; (d) mixing a particle blocking solution including a blocking agent with the mixture in step (c) at room temperature for a time sufficient for the blocking agent to bind sites on the particles not bound to the EPS or LPS; and (e) applying the mixture of step (d) to the sample pad in the detection apparatus at room temperature, wherein presence of the microorganism in the material is indicated by a visible signal produced by binding of the EPS or LPS bound to the particles by the antibody specific for the EPS or LPS immobilized in the detection zone.

In a preferred embodiment of the above method, the membrane further includes a reference zone laterally spaced between the detection zone and the wicking pad in which is immobilized therein a control antibody and the particle blocking solution further includes particles which have bound thereon an antigen which binds the control antibody.

In a preferred embodiment of the above method, the particles are polystyrene latex particles which preferably have a diameter from about 0.06 μm to 1.0 μm, most preferably, a diameter of about 0.77 μm.

Preferably, in the above method the CTAB is at a concentration between about 0.25% and 2% and the salt is NaCl at a concentration of about 2% in a buffer such as 2 mM Tris HCl, pH 9.2.

In a further embodiment of the above method, the particle blocking agent is bovine serum albumin. Preferably, the particle blocking solution includes bovine serum albumin and polysorbate 20 in a buffer and most preferably, the particle blocking solution includes bovine serum albumin, polysorbate 20, and n-dodecyl-N,N-dimethyl glycine in a buffer.

In a further embodiment of the above method, the membrane is a nitrocellulose membrane, preferably a nitrocellulose membrane which has a pore size from about 10 to 20 μm, most preferably, a pore size of about 15 μm. In a further embodiment, the membrane has been treated with a blocking agent, preferably, a blocking agent such as bovine serum albumin.

In a further embodiment of the above method, the sample pad includes a polyester or glass fibers which preferably has been treated with a blocking agent which is preferably selected from the group consisting of bovine serum albumin, non-fat dry milk, and mixtures thereof.

In a further embodiment of the above method, the wicking pad includes a cellulosic material.

In a further embodiment of the above method, the material is a plant material or the material is serum or tissue from an animal or human.

In a further embodiment of the present invention, the present invention provides a kit for detecting EPS, LPS, or both, produced by a microorganism, which comprises (a) providing a detection apparatus which includes mounted on a support member an elongated membrane having a first end and a second end wherein in lateral contact with the first end of the membrane is a sample pad for receiving a liquid sample and in lateral contact with the second end of the membrane is a wicking pad which allows the liquid sample to flow through the membrane from the sample pad to the wicking pad and wherein the membrane further comprises at least one detection zone laterally spaced from the sample pad in which is immobilized an antibody which is specific for the EPS or LPS; (b) a first container containing an extraction solution; (c) a second container containing a particle blocking solution; and (d) a third container containing a suspension including particles, preferably colored, which are capable of binding of the EPS and LPS.

Preferably, the membrane further includes a reference zone laterally spaced between the detection zone and the wicking pad in which is immobilized therein a control antibody and the particle blocking solution further includes particles which have bound thereon an antigen which binds the control antibody.

In a preferred embodiment of the kit, the particles in the third container and comprising the control antibody are polystyrene latex particles.

It is further preferable that the second and third containers are dropper bottles.

It is further preferable that the extraction solution includes cetyltrimethylammonium bromide (CTAB) in a high salt buffer.

In a further preferred embodiment of the kit, the membrane is a nitrocellulose membrane. Preferably, a membrane which has been treated with a blocking agent.

In a further preferred embodiment of the kit, the sample pad includes a polyester or glass fibers and the wicking pad includes a cellulosic material.

In a further embodiment of the kit, the particle blocking solution includes bovine serum albumin.

In a further embodiment of the present invention, the present invention provides a method for detecting the presence of an infection in a plant caused by a virus selected from the group consisting of potyviridae and tobamoviridae, which comprises (a) providing a detection apparatus which includes mounted on a support member an elongated membrane having a first end and a second end wherein in lateral contact with the first end of the membrane is a sample pad for receiving a liquid sample and in lateral contact with the second end of the membrane is a wicking pad which allows the liquid sample to flow through the membrane from the sample pad to the wicking pad and wherein the membrane further comprises at least one detection zone laterally spaced from the sample pad in which is immobilized an antibody which is specific for a protein of the virus and a reference zone laterally spaced between the detection zone and the wicking pad in which is immobilized a control antibody; (b) mixing a material from the plant with an extraction solution for a time sufficient to produce a mixture including the virus proteins; (c) mixing an aliquot of the mixture with particles, preferably colored, at room temperature for a time sufficient to preferentially bind the protein of the virus to the particles without substantial binding of other components of the mixture to the particles; (d) mixing a solution including a blocking agent with the mixture in step (c) at room temperature for a time sufficient to block sites on the particles not bound to the proteins of the virus; and (e) applying the mixture with the particles bound to the protein of the virus and the blocking agent to the sample pad in the detection apparatus at room temperature wherein binding of the protein of the particles bound by the antibody specific for the protein immobilized in the detection zone indicates the presence of the infection.

In a preferred embodiment of the above method, the particles are polystyrene latex particles which preferably have a diameter from about 0.06 µm to 1.0 µm, most preferably, a diameter of about 0.77 µm.

In a further embodiment of the above method, the extraction solution includes a carbonate-bicarbonate buffer, preferably at a pH of about 9.6.

In a further embodiment of the above method, the particle blocking agent is bovine serum albumin. Preferably, the particle blocking solution includes bovine serum albumin and polysorbate 20 in a buffer and most preferably, the particle blocking solution includes bovine serum albumin, polysorbate 20, and n-dodecyl-N,N-dimethyl glycine in a buffer.

In a further embodiment of the above method, the membrane is a nitrocellulose membrane, preferably a nitrocellulose membrane which has a pore size from about 10 to 20 µm, most preferably, a pore size of about 15 µm. In a further embodiment, the membrane has been treated with a blocking agent, preferably, a blocking agent such as bovine serum albumin.

In a further embodiment of the above method, the sample pad includes a polyester or glass fibers which preferably has been treated with a blocking agent which is preferably selected from the group consisting of bovine serum albumin, non-fat dry milk, and mixtures thereof.

In a further embodiment of the present invention, the present invention provides a kit for detecting virus proteins produced by a virus selected from the group consisting of potyviridae and tobamoviridae, which comprises (a) providing a detection apparatus which includes mounted on a support member an elongated membrane having a first end and a second end wherein in lateral contact with the first end of the membrane is a sample pad for receiving a liquid sample and in lateral contact with the second end of the membrane is a wicking pad which allows the liquid sample to flow through the membrane from the sample pad to the wicking pad and wherein the membrane further comprises at least one detection zone laterally spaced from the sample pad in which is immobilized an antibody which is specific for the virus protein; (b) a first container containing an extraction solution; (c) a second container containing a particle blocking solution; and (d) a third container containing a suspension including particles, preferably colored, which are capable of binding of the virus proteins.

Preferably, the membrane further includes a reference zone laterally spaced between the detection zone and the wicking pad in which is immobilized therein a control antibody and the particle blocking solution further includes particles which have bound thereon an antigen which binds the control antibody.

In a preferred embodiment of the kit, the particles in the third container and comprising the control antibody are polystyrene latex particles.

It is further preferable that the second and third containers are dropper bottles.

In a further preferred embodiment of the kit, the membrane is a nitrocellulose membrane. Preferably, a membrane which has been treated with a blocking agent.

In a further preferred embodiment of the kit, the sample pad includes a polyester or glass fibers and the wicking pad includes a cellulosic material.

In a further embodiment of the kit, the particle blocking solution includes bovine serum albumin.

Therefore, in view of the above, the present invention provides a method for determining whether a material contains an analyte, which comprises (a) providing a detection apparatus which includes mounted on a support member an elongated membrane having a first end and a second end wherein in lateral contact with the first end of the membrane is a sample pad for receiving a liquid sample and in lateral contact with the second end of the membrane is a wicking pad which allows the liquid sample to flow through the membrane from the sample pad to the wicking pad and wherein the membrane further comprises at least one detection zone laterally spaced from the sample pad in which is immobilized a binding member specific for the analyte; (b) mixing the material with an extraction solution to produce a mixture including the analyte; (c) mixing an aliquot of the mixture in step (b) with colored particles at room temperature for a time sufficient for the particles to bind a sufficient quantity of the analyte sufficient for detection of the colored particles in the detection zone; (d) mixing a particle blocking solution including a blocking agent with the mixture in step (c) at room temperature for a time sufficient to block sites on the particles not bound to the analyte; and (e) applying the mixture with the particles bound to the analyte and the blocking agent to the sample pad in the detection apparatus at room temperature wherein binding of the analyte bound to the particles bound by the binding member specific for the analyte immobilized in the detection zone indicates the presence of the analyte in the material.

Further in view of the above, the present invention provides a kit for detecting an analyte, which comprises (a) providing a detection apparatus which includes mounted on a support member an elongated membrane having a first end and a second end wherein in lateral contact with the first end of the membrane is a sample pad for receiving a liquid sample and in lateral contact with the second end of the membrane is a wicking pad which allows the liquid sample to flow through the membrane from the sample pad to the wicking pad and wherein the membrane further comprises at least one detection zone laterally spaced from the sample pad in which is immobilized an antibody which is specific for the analyte; (b) a first container containing an extraction solution; (c) a second container containing a particle blocking solution; and (d) a third container containing a suspension including particles which are capable of binding of the analyte.

Preferably, in the above method and kit, the analyte is selected from the group consisting of protein, polysaccharide, and chemical. Preferably, the protein is selected from the group consisting of viral protein, bacterial protein, immunoglobulin, parasite protein, plant protein, mammalian protein, hormone, and insect protein. Preferably, the polysaccharide is selected from the group consisting of extracellular polysaccharides (EPS), lipopolysaccharides (LPS), and mixtures thereof. Preferably, the chemical is selected from the group consisting of herbicide, pesticide, drug, hormone, and derivative thereof. The method and kit for detecting bacterial EPS or LPS or the above viral proteins are included in the above method and kit for detecting an analyte.

OBJECTS

The object of the present invention is to provide a simple to use, field-based immunoassay for detecting important pathogenic microorganisms which infect plants and animals, including humans, and which produce EPS or LPS by using species-specific antibodies specific for EPS or LPS.

It is a further object of the present invention to provide the assay in a format based on immunostrip chromatography.

It is a further object of the present invention that the immunoassay be able to detect the microorganism in a sample from a plant or animal without killing the microorganism in the sample thus, enabling the microorganism in the sample to be cultured for further analysis.

It is a further object of the present invention to provide an immunoassay for detecting viruses in a plant material.

These and other objects of the present invention will become increasingly apparent with reference to the following drawings and preferred embodiments.

DESCRIPTION OF THE DRAWINGS

FIG. 1b shows a plan view of the immunostrip 10 of FIG. 1a.

DETAILED DESCRIPTION OF THE INVENTION

Figure 1A:
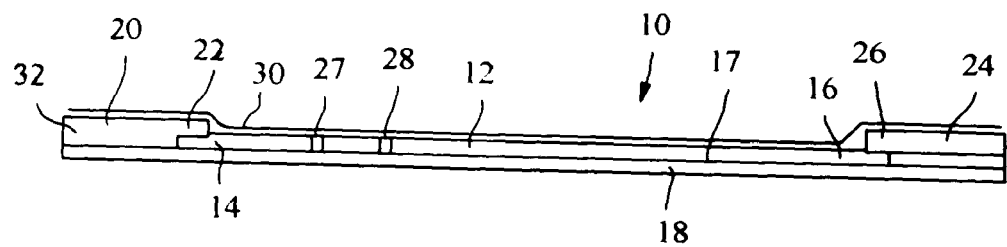
FIG. 1a shows a side view of an immunostrip 10.

All patents, patent applications, government publications, government regulations, and literature references cited in this specification are hereby incorporated herein by reference in their entirety. In case of conflict, the present description, including definitions, will control.

As used herein, the term "extracellular polysaccharide (EPS)" includes the terms "exocellular polysaccharide", "capsule", and "lipopolysaccharide (LPS)". All bacteria produce extracellular polysaccharides to an extent with the amount is produced dependent on the nutritional source for the bacteria. However, LPS is produced only by Gram-negative bacteria. In other words, a Gram-negative bacterial capsule contains both EPS and LPS (detached). The present invention can include in an assay polyclonal or monoclonal antibodies against either EPS or LPS or both EPS and LPS.

The present invention provides a method based on lateral flow immunochromatography for detecting the presence of an analyte in a liquid sample. The method is a direct immunoassay method which is particularly suited for determining whether a material or organism is infected with particular pathogenic bacteria by detecting species specific extracellular polysaccharides (EPS), lipopolysaccharides (LPS), or both, produced by the pathogenic bacteria or particular proteins produced by particular groups of viruses. While the method is useful for determining whether a plant material is infected with particular EPS- or LPS-producing bacteria or a particular virus from the potyvirus group, the method is also useful for determining the presence of EPS, LPS, or both, in the serum or tissue of an animal or human host and the presence of antigens produced by other pathogens which infect humans, animals, and plants. In the case of an animal or human host, the method enables detection of bacteremia and septicemia in the host at an early stage of infection when the prognosis for treating the infection is more favorable.

The method of the present invention comprises a lateral flow immunochromatography apparatus (hereinafter "immunostrip") comprising a detection zone for capturing an analyte or antigen in a sample and polystyrene latex particles for binding the analyte in the sample. Preferably, the polystyrene latex particles are colored with a dye or the like which renders the particles visible to the human eye in visible light. This enables visualization of the analyte captured in the detection zone by the human eye or a machine reader. However, the particles can be "colored" by other means such as labeling the particles with a fluorescent dye or the like which produces a fluorescent signal when illuminated with an ultraviolet light which can also be detected by the human eye or a machine reader. Examples of analytes which can be bound include, but are not limited to, EPS, LPS, immunoglobulins such as IgG, IgM, IgA, or IgE, plant and animal hormones, bacterial proteins, recombinant proteins, viral proteins, organic chemicals, drugs and derivatives thereof, various cytological markers. The method takes advantage of the phenomenon wherein in a mixture of macromolecules containing particular analytes or antigens such as EPS, LPS, or particular viral proteins, the EPS, LPS, or particular viral proteins will preferentially adsorb or bind to polystyrene latex, in general, at a rate faster than the rate for other components in the mixture. Thus, by exposing polystyrene latex particles to the mixture of macromolecules for a short period of time, polystyrene latex particles are obtained which are absorbed or bound with the particular analyte such as EPS, LPS, or particular viral proteins. In the case of analytes or antigens such as EPS, LPS, and particular virus proteins, in a short exposure period, the antigens are preferentially adsorbed or bound to the polystyrene latex particles without substantial binding of the other components of the mixture. The method enables detection of an analyte as long as the quantity of the analyte in the sample is enough to bind a sufficient number of the particles to enable visualization of the particles bound to analyte when captured by the detection zone of the immunostrip. The method is also useful for detecting analytes which do not preferentially bind to polystyrene latex. For such analytes, the incubation time of the sample with the polystyrene latex particles can be increased to ensure that a sufficient quantity of the particles are bound to the analyte.

Preferably, after adsorbing or binding the analyte to the polystyrene latex particles and before applying to the immunostrip, the polystyrene latex particles are treated with a protein or detergent to bind sites on the polystyrene latex particles not bound by the analyte. The polystyrene latex particles are then applied to the immunostrip and allowed to flow into the immunostrip to a detection zone on the immunostrip which comprises immobilized thereat an antibody which is specific for the analyte. The immobilized antibody captures the analyte adsorbed or bound to the polystyrene latex particles which is detectable by virtue of the coloring of the polystyrene latex particles.

The method is a direct immunoassay method. The absence of visible signal or color or fluorescence at the detection zone indicates that the sample does not contain the analyte. Conversely, the presence of signal or color or fluorescence at the detection zone indicates that the sample contains the analyte.

The greater the intensity of the signal or color or fluorescence at the detection zone, the greater the concentration of analyte in the sample.

Unlike many conventional immunostrips, the method of the present invention uses the colored polystyrene latex particles to bind the analyte in solution which labels the analyte. The method does not require a labeled antibody specific for the analyte or for the complex formed between the analyte and the immobilized capture antibody or an antibody coupled to the polystyrene latex particles to bind the analyte. Thus, "naked" colored polystyrene latex particles are used to bind the analyte which labels the analyte for subsequent detection by lateral flow chromatography. Furthermore, the present method does not require a coupling reaction to covalently link the analyte to reactive groups such as carboxy, tosyl, or amine groups on the surface of the polystyrene latex particle. Therefore, the present method does not require multiple antibodies, conjugated antibodies, coupling reactions, or subsequent reaction steps following the immunochromagraphic step for visualizing the captured analyte. The method of the present invention provides a simple direct immunochromatography method for detecting the presence of an analyte which uses colored polystyrene latex particles for both binding the analyte and for detecting the analyte when bound by the antibody in the detection zone of the immunostrip. The simplicity of the method simplifies manufacture of kits for performing the method because the only component of the kit which must be specific for a particular analyte is the antibody immobilized at the detection zone.

The method is particularly suited for the detection of EPS or LPS produced by pathogenic bacteria. The envelope (or capsule) of many pathogenic bacteria, and a number of plant pathogenic bacteria in particular, contain high molecular weight, extracellular polysaccharides (EPS), which are hydrophilic and usually acidic (Denny, Ann. Rev. Phytopathol. 33: 173-97. (1995)). In addition to EPS, the bacterial capsule can contain lipopolysaccharide (LPS) O-antigen and several small subunits of β-glucans. LPS is composed of lipid A and a hydrophilic polysaccharide moiety, which contains a core with O-antigen side chains. LPS is a major constituent of the cell walls of gram-negative bacteria, and are recognized as the active component of gram-negative bacterial endotoxins. In mammals, endotoxins exhibit a variety of pathophysiological effects including septic shock. These EPS and O-antigen molecules are also of taxonomic importance due to their variability among species and strains (Goto, In: Fundamentals of Bacterial Plant Pathology, Academic Press, New York (1990)).

Monoclonal antibodies with species specificity can be produced using these bacterial capsule components as antigens (Alvarez et al., Plant Dis. 69: 1022-1026 (1985); Alvarez et al., Phytopathol. 75: 722-728 (1985); Alvarez et al., Phytopathol. 81: 857-865 (1991); Alvarez et al., In: Bacterial Wilt International Conf., Kaohsiung, Taiwan, ACIAR Proc. No. 45 (1992), pp. 62-69; Alvarez et al., Plant Pathol. 45: 358-366 (1996); Alvarez et al., In: Seed Health Testing: Progress towards the 21st Century., Hutchins and Reeves, Eds., CAB International, Wallingford, United Kingdom (1998) pp. 175-183; Alvarez et al., In Proc. $3^{rd}$. International Seed Testing Association, Seed Health Symposium, Iowa State University, Ames, Iowa (1999), pp. 110-114; Hampton, In: Serological Methods for Detection and Identification of Viral and Bacterial Plant Pathogens, a Laboratory Manual. APS Press, St. Paul, Minn. (1990); and several small subunits of β-glucans. For example, several bacterial plant pathogens belonging to genera *Ralstonium, Pseudomonas , Calvibacter, Erwinia, Xanthomonas* cause a majority of the known bacterial diseases of crops, vegetables, ornamental and fruit trees. These bacteria produce copious amounts of EPS during pathogenesis (Denny, Ann. Rev. Phytopathol. 33: 173-97 (1995)) which suggested that the EPS might be useful as a diagnostic marker for detecting these bacteria. In the case of *R. solanacearum*, antibody PS1 was produced against an epitope in the *R. solanacearum* EPS (McGarvey et al., In: Bacterial Wilt Disease: Molecular and Ecological Aspects. Prior et al. Eds., Proceedings of the Second International Bacterial Wilt Symposium. Springer-Verlag, Berlin (1998), pp. 157-163).

EPS might provide a selective advantage for the pathogenic plant bacteria. EPS might (1) aid the bacteria in attachment to the host surface, (2) protect bacteria from desiccation, (3) improve nutrient uptake and retention, (4) reduce contact with host defense molecules, (5) aid in symptom development, (6) aid in movement of bacteria through vesicles, or (7) have a role in virulence (Denny, Ann. Rev. Phytopathol. 33: 173-97 (1995)). For example, EPS has been shown to have a major role in disease and symptom expression of bacterial pathogens such as *R. solanacearum* (Cook, J. Bacteriol. 173: 1654-62 (1991); Denny, Ann. Rev. Phytopathol. 33: 173-97 (1995)), Cmm in alfalfa and potato (Bishop, Potato Res. 35: 59-63 (1992)), *E. amylovora* in apple and pear (Geicer and Geider, Physiol. Mol. Plant Pathol. 42: 387-404 (1993)) and *Pantoea stewarti* in corn (Leigh and Coplin, Ann. Rev. Microbiol. 46: 307-46 (1992)). Therefore, in an infected symptomatic plant, EPS would be present in sufficient quantities to enable it to be detected immunologically.

Mutational studies of several bacterial pathogens have also shown that while non-mucoid, EPS negative mutants may still infect the host, they poorly colonize it (Denny, Ann. Rev. Phytopathol. 33: 173-97 (1995); Genin and Boucher, Mol. Plant Pathol. 3: 111-118 (2002); Araud-Razous et al., Eur. J. Plant Pathol. 104: 795-809 (1998); Saile et al., Phytopathol. 87: 1264-1271 (1997)). In the initial stage of infection, bacteria may produce little or no EPS due to an auto-induction or a quorum-sensing mechanism; therefore, high levels of EPS may not interfere with the mechanism of recognition of pathogenesis (Beck von Bodman, Proc. Natl. Acad. Sci. USA 95: 7687-7692 (1998)). However, once the host tissue has been successfully colonized, the genes responsible for production of EPS are activated and copious amounts of EPS are produced. In certain bacterial wilt infections, translocated EPS was detected in apical plant tissue with no bacterial presence. The above suggests that removing EPS or LPS from bacteria does not kill the bacteria.

In *R. solanacearum*, a transcriptional regulator called PhcA (Brumbley et al., J. Bacteriol. 175: 5477-5487 (1993)) regulates the cell density-sensing system. This quorum-sensing molecule activates a set of virulence genes, including EPS production, and suppresses the genes involved in motility, synthesis of cell wall degrading enzymes, and synthesis of siderophores. Mutations in phcA result in morphological changes called "phenotypic conversion" (PC). A saprophytic survival type (PC type) and a pathogenic type (wild-type) shift is speculated for *R. solanacearum* (Denny et al., In: Bacterial Wilt: the Disease and its Causative Agent, *Pseudomonas solanacearum*, Hayward and Hartman, Eds., CAB International, Oxon, United Kingdom, (1994), pp. 137-143). Thus, the bacterium always produces EPS once it colonizes the plant. Therefore, using EPS as a target antigen to detect *R. solanacearum* infections in plants is a particularly effective.

In a recent study, Alvarez and Kanshero (In: Proc. $3^{rd}$ Intl. Seed testing Assoc., Seed Health Symp. Iowa State University, Ames, Iowa (1999), pp. 93-97) compared the utility of monoclonal antibodies produced against EPS of *C. michigan*-

*ensis* subsp. *michiganensis* to PCR-based assays. They concluded that assays based on these antibodies have a specificity superior to PCR-based assays. Other analyses showed that the performance of anti-*R. solanacearum* EPS antibodies was at least equal to the performance of PCR-based assays (Schoedel and Sutula, Poster presented at American Phytopathol. Society annual meetings, Madison, Wis. (2002)).

EPS are high-molecular-weight polysaccharides (greater than 100,000 Da), anionic, and hydrophilic. EPS are hydrophilic, anionic, high-molecular-weight polysaccharides with repeating sugar units and are usually found as polymers or large aggregates. Many bacteria, including pathogens of humans, livestock, and plants produce copious amounts of EPS. However, LPS is present only in Gram-negative bacteria and is commonly referred as endotoxin. LPS form the outermost layer of Gram-negative bacteria and contains (1) lipid A, (2) an oligosaccharide core region, and (3) O-chains consisting of repeating oligosaccharides or sugars. LPS is anionic due to the phospholipid groups and readily binds to cationic molecules and is amphiphilic. Lipid A is highly conserved among Gram-negative bacteria anchors the LPS to the bacterial cell membrane and is hydrophobic. The O-chain also known as O antigen is hydrophilic and great variation occurs in the composition of the sugars in the O side chain between species and even strains of Gram-negative bacteria. LPS is toxic to mammals and causes bacteremia and septicemia. Among plant infecting bacteria LPS is involved in defense, host recognition and symptom development. Often LPS is secreted into the outer capsule. Thus a bacterial capsule of gram-negative bacteria contain both EPS and LPS.

Both LPS and EPS are anionic and readily bind to a cationic detergent like CTAB (Cetyl Trimethyl Ammonium Bromide) to form aggregates. Also, both EPS and LPS are resistant to boiling for a brief period of time. These two principles were used to develop the method herein for detecting bacterial infections in plants. One method involves boiling of the bacterial ooze or suspension in TBSE at 100° C. for 10 minutes. This procedure destroys all the proteins from host and bacteria and retains the EPS and LPS antigens. Once free from the membrane, LPS may form aggregates due to the hydrophobicity of lipid A portion as micelles. The other method involves precipitation of EPS and LPS by with CTAB in a buffer such as TBS buffer. This results in formation of large aggregates EPS or LPS, a "selective enrichment" of antigen in a sample.

Without intending to be bound by any particular theory, the adsorption of these polysaccharides to polystyrene is primarily due to van der Waals forces due to the stationary polarity (SP) and forces due to alternating polarity (AP), which are hydrophobic and secondarily due to ionic interactions. Polystyrene latex particles are usually manufactured by emulsion polymerization using an anionic surfactant and the particles so produced contain sulfate groups ($SO^{3-}$) on the surface derived from the polymerization initiator (Seradyn Inc., technical bulletin, February 1999). Van der Waals forces mediated bonds are usually weak and a large number of the bonds are required to form stable complexes or aggregates. Therefore, the larger the molecular aggregate or complex, the stronger and faster is the binding. EPS and LPS, because of their high molecular weight and their ability to form complexes, bind to polystyrene rapidly due to ionic interactions compared to other host proteins which might be present in the sample. LPS, because of its amphiphilic nature, readily binds to polystyrene due to hydrophobic interactions as well. The addition of CTAB, a cationic detergent, augments the binding of anionic EPS and LPS to polystyrene by (1) forming large aggregates which increases the number of intermolecular interactions available between the EPS or LPS and the polystyrene and (2) bringing the aggregates (cationic CTAB-EPS/LPS complexes) to the anionic polystyrene.

Using the above principle, the present invention provides bacterial diagnostic assays to identify EPS-producing pathogenic and non-pathogenic bacteria. Examples of such pathogenic EPS-producing bacteria which infect plants include, but are not limited to, bacteria such as *Acidovorax avenae* subsp. *citrulli, Acinetobacter calcoacaticus, Bacillus cerelis, Bacillus subtilis, Curtobacterium flaccumfaciens* pv *poinsettiae, Clavibacter michiganensis* subsp. *insidiosus, Clavibacter michiganensis* subsp. *michiganensis, Clavibacter michiganensis* subsp. *nebraskensis, Clavibacter poinsettiae, Clavibacter michiganensis* subsp. *sepedonicus, Clavibacter michiganensis* subsp. *tessellarius, Erwinia carotovora* subsp. *atroseptica, Erwinia carotovora* subsp. *carotovora, Erwinia carotovora* subsp. *chrysanthemi, Erwinia herbicola, Erwinia stewartii, Pseudomonas aeringimosa, Pseudomonas avenae, Pseudomonas fuscovaginae, Pseudomonas glumae, Pseudomonas fluorescens, Pseudomonas syringae* pv *phaseolicola, Pseudomonas putida, Pseudomonas syringae* pv *glycincae, Pseudomonas syringae* pv *tomato, Ralstonia solanacearum, Serritia marcesens, Streptococcus aurelius, Streptococcus faecalis, Xanthomonas albilineans, Xanthomonas campestris* pv. *armoraciae, Xanthomonas campestris* pv. *begoniae, Xanthomonas campestris* pv. *campestris, Xanthomonas campestris* pv. *citri, Xanthomonas campestris* pv. *dieffenbachiae, Xanthomonas campestris* pv. *oryzae, Xanthomonas campestris* pv. *pelargonii, Xanthomonas campestris* pv. *phaseoli, Xanthomonas campestris* pv *transluciens, Xanthomonas campestris* pv *vesicatora, Xanthomonas campestris* pv *zinnea, Xanthomonas maltophilia*, and the like. Among the plant pathogenic bacteria, species belonging to the genera *Erwinia, Pantoea, Acidovorax, Pseudomonas, Ralstonia, Burkholderia, Xylophilus, Xanthomonas* and *Agrobacterium* belong to Gram-negative group and contain LPS on their outer membrane in addition to EPS. The present invention also provides diagnostic assays for detecting EPS producing fungi. The present invention also provides bacterial diagnostic assays for identifying EPS-producing bacteria and LPS-producing gram negative bacteria which might be present in serum or tissue from animal or human hosts, milk, feedstock, food, and cultures prepared therefrom. These bacteria include, but are not limited to, *Acinetobacter* spp., *Actinobacillus* spp. such as *A. pleuropheumoniae, Bordetella* spp. such as *B. pertussis, Citrobacter* spp., *Enterobacter* spp., *Escherichia coli* types, *Haemophilus* spp. such as *H. influenzae, Klebsiella* spp., *Legionella* spp. such as *L. pneumophila, Moraxella* spp. such as *M. catarrhalis, Neisseria* spp. such as *N. gonorrhoeae*, Proteus spp. such as *P. mirabilis, Providencia* spp., *Pseudomonas* spp., *Samonella* spp., *Serratia* spp., *Shigella* spp., *Yersinia* spp. such as *Y. enterocolitica*, and the like. The above bacteria can be identified in aliquots prepared from symptomatic tissue or fluids in about 10 to 30 minutes of assay time. The principle of the assay is based on the rapid binding of the EPS or LPS to the treated polystyrene and specific polyclonal or monoclonal antibodies produced against the EPS or LPS of the bacterium which are pathovar/subspecies specific.

Thus, in one embodiment, the present invention provides a method for detecting EPS or LPS in a sample comprising a lateral flow immunochromatography apparatus (hereinafter "immunostrip") and colored polystyrene latex particles for adsorbing or binding EPS or LPS in the sample. Preferably, after adsorbing or binding the EPS or LPS to the polystyrene latex particles and before applying the polystyrene latex particles bound to the EPS or LPS to the immunostrip, the polystyrene latex particles are treated with blocking agent such as a protein or detergent to quench unoccupied binding sites. The protein or detergent binds to sites on the polystyrene latex particles not bound to EPS or LPS. This prevents binding of the sites on the polystyrene latex particles not bound by EPS or LPS from binding other components in the sample and from binding to the antibody immobilized in the detection zone. The polystyrene latex particles are then applied to the immunostrip and allowed to flow into the immunostrip to a detection zone on the immunostrip which comprises immobilized thereat an antibody, preferably a monoclonal antibody, which is specific for the EPS or LPS.

Figure 1B:
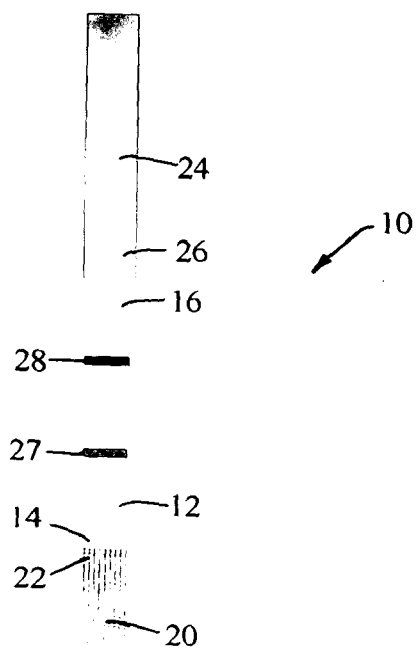

FIGS. 1a and 1b illustrate a side view and a plan view, respectively, of an embodiment of a lateral flow immunochromatography apparatus (hereinafter "immunostrip" or "ACL strip") suitable for practicing the method of the present invention. As shown in FIG. 1a, the immunostrip 10 comprises an elongated membrane 12 with a first end 14 and a second end 16 mounted onto the upper surface 17 of a support member 18. The membrane 12 can comprise any material which will enable both the flow of polystyrene latex particles with an average particle diameter of about from about 0.06 µm to 1.0 µm, preferably 0.77 µm, and the immobilization of a sufficient quantity of antibody in the detection zone 27 and the optional reference (or control) zone 28. In particular embodiments, the reference zone 28 can have immobilized thereat a reagent for detecting a component in the solution containing the sample such as a pH indicator. Preferably, the membrane 12 comprising the immunostrip 10 comprises nitrocellulose having an average pore size between about 10 and 20 µm, most preferably, the pore size of the nitrocellulose is about 15 µm. The support member 18 can be made from any material which is impervious to aqueous solutions such as a polymer or polymer coated card stock. A preferred support member 18 comprises a card stock coated with a polymer such as polyvinyl or the like.

In lateral contact with the membrane 12 at its first end 14 and mounted on the upper surface 17 of the support member 18, is a sample pad 20. Preferably, as shown in FIG. 1a, the second end 22 of the sample pad 20 partially overlaps the first end 14 of the membrane 12. The sample pad 20 can comprise any liquid absorbent material such as a polymer such as polyester or glass fiber filter material with a pore size sufficient to enable particles from about 0.06 µm to 1.0 µm in diameter to pass or flow through substantially unhindered. A preferred material for the sample pad 20 comprises glass fibers such as in the Millipore GFCP203000 glass fiber filter. Preferably, the sample pad 20 is treated with a blocking solution containing a protein and optionally a carbohydrate and then dried. The blocking solution facilitates flow of the polystyrene latex particles through the sample pad 20 to the membrane 12. For example, the glass fiber filter material is soaked in a phosphate buffered saline solution, containing 2% bovine serum albumin and 2% polyoxyethylenesorbitan monolaurate (polysorbate 20 or TWEEN-20) and then dried at room temperature or an elevated temperature such as 37° C. Other formulations for blocking solutions which can be used for treating the sample pad 20 would be readily apparent to one skilled in the art.

In lateral contact with the membrane 12 at its second end 16 and mounted on the upper surface 17 of the support member 18 is a wicking pad 24. Preferably, as shown in FIG. 1a, the first end 26 of the wicking pad 24 partially overlaps the second end 16 of the membrane 12. The wicking pad 24 can comprise any high-capacity hydrophilic material capable of absorbing liquid such as cellulose fibers, a cellulose sponge, or the like. Alternatively, in lieu of the wicking pad 24, the membrane 12 can be of sufficient absorbent capacity as to enable the required flow of the sample from the sample pad 20 through a portion of the membrane 12 which includes the detection zone 27 and the optional reference zone 28.

Laterally spaced from the sample pad 22 and on the membrane 12 is a detection zone 27 in which is immobilized an antibody, preferably a monoclonal antibody, specific for the analyte. In particular embodiments (not shown), the membrane 12 can have disposed thereon more than one detection zone 27, each containing an antibody species capable of binding a particular analyte. FIG. 1a also shows laterally spaced from the detection zone 27 an optional reference zone 28 in which is immobilized one member of a binding pair capable of binding a control analyte, preferably the one member of the binding pair is an antibody or monoclonal antibody specific for the control analyte, or a reagent for detecting a component in the sample buffer such as a pH indicator. Each antibody is provided as a solution which is preferably at concentration of about 0.5 to 1 mg/mL which is then applied to the appropriate zone at about 0.6 µL/cm to 0.75 µL/cm as a narrow line parallel to the width of the membrane 12. For particular monoclonal antibody preparations the signal-to-noise ratio is improved by partially purifying the monoclonal antibody by ammonium sulfate precipitation. After the antibody has been applied to the membrane 12, the membrane 12 is dried at room temperature or an elevated temperature such as 37° C. for a time sufficient to immobilize the antibody to the membrane 12. In general, drying the membrane 12 for 2 to 3 hours at 37° C. is sufficient. Next, it is preferable that the membrane 12 with the antibody immobilized thereon is blocked with a blocking solution containing a protein or a detergent, or both. An example of such a blocking solution is 2% bovine serum albumin in water or a surfactant such as polysorbate 20 (TWEEN 20). A preferred blocking solution comprises 2% bovine serum albumin in a buffer such as phosphate buffered saline. The blocking solution facilitates flow of the polystyrene latex particles through the membrane 12 and improves the signal-to-noise ratio. After blocking, the membrane 12 is dried at room temperature or an elevated temperature such as 37° C.

FIG. 1b shows a plan view of the immunostrip 10 which shows the membrane 12 with the second end 22 of the sample pad 20 in lateral contact with the first end 14 of the membrane 12 and the first end 26 of the wicking pad 24 in lateral contact with the second end 16 of the membrane 12. Also shown is the detection zone 27 and the optional reference zone 28.

After the immunostrip 10 has been assembled and the detection zone 27 and the optional reference zone 28 applied to the membrane 12 and dried and the membrane 12 blocked with blocking solution and dried, the immunostrip is preferably covered with a light transparent polymer film 30 such that only about 1 to 3 mm of the first end 32 of the sample pad 20 remains uncovered (as shown in FIG. 1a).

Detection of analyte is effected by colored polystyrene latex particles which render the particles visible to the human eye or a machine reader, particularly when a multiplicity of the particles are bound by the antibody in the detection zone. As used herein, the term "colored" includes dyes which are visible in visible light, dyes which are fluorescent under ultraviolet light, and dyes which are both. Preferred polystyrene latex particles are made by emulsion polymerization and have a sphere diameter from about 0.06 µm to 1.0 µm, preferably, about 0.77 µm (±0.03 µm). The particles are dyed by a dye impregnation process wherein the particles are swollen in an organic solvent containing a water-insoluble dye. The dye diffuses into the particles and are trapped within the particles when they shrink as the solvent is removed by evaporation or multiple washings in an aqueous solution. The amount of dye incorporated into the particles ranges from about 10 to 40% based on the weight of the particles.

Polystyrene latex particles colored by methods other than that disclosed above are expected to be suitable for use in the present invention as long as the coloring method does not interfere with the ability of the particles to adsorb or bind EPS and LPS or proteins produced by particular groups of viruses. Furthermore, it has been found that colored polystyrene latex particles which have been modified to contain reactive groups for covalent attachment of proteins or nucleic acids are also suitable for use in the present invention even though in the present invention, the analyte is not covalently attached to the particles. Examples of such modified polystyrene latex particles include those which have been modified to include carboxyl, amino, or tosyl groups for binding proteins.

The general method for detecting EPS or LPS produced by bacteria is as follows. A sample from an organism suspected of being infected with bacteria which produces EPS or LPS is provided as a liquid extract. For example, in the case of testing a plant tissue for infection by the bacteria, the tissue is placed into an aqueous buffer solution such as TBSE buffer (2 mM Tris HCl, pH 9.2, 2% NaCl, and 0.01% EDTA) or the like, or water. When an infected tissue is cut and soaked or ground in the aqueous buffer solution or water, the bacteria along with EPS capsule ooze out into the aqueous buffer solution or water. For example, about $10^6$ to $10^9$ bacteria per mL can be obtained in a short period of time when a tissue containing a leaf spot is soaked in a vial of water or phosphate buffered saline.

A sample treatment can be included at this stage to enhance the extraction of EPS and/or LPS. For example, boiling such a sample at 100° C. for 10 minutes kills the bacteria and destroys most of the bacterial and host proteins and liberates EPS and LPS. While boiling the sample enhances the extraction of EPS and LPS, the method kills the bacteria and most proteins which prevents confirmation of the results of the immunostrip assay by subsequent analytical methods such as culturing the bacteria. Furthermore, because a means for boiling the sample is required, extraction based on boiling is impractical for field use.

It was discovered that the cationic detergent cetyltrimethylammonium bromide (CTAB) can selectively enhance the extraction of EPS and LPS without apparent killing of the bacteria and destruction of the host and bacterial proteins. CTAB has been widely used by molecular biologists for selectively purifying DNA from contaminating polysaccharides which might be present in particular strains of bacteria or plant tissue. Most DNA purification methods which use CTAB selectively precipitate DNA from lysed cells using CTAB in a high salt buffer. It was discovered that EPS (or LPS) can be selectively extracted from solutions containing unlysed bacteria under ambient conditions by incubating the unlysed bacteria in a high salt solution at a physiological pH containing CTAB (CTAB extraction buffer). The CTAB binds to anionic EPS and LPS to form large macromolecular aggregates which then appear to form a fine precipitate in the extraction buffer. The concentration of CTAB useful for extracting EPS or LPS can range from about 0.25% to 2%; however, the preferred concentration is about 0.5%. The preferred high salt solution comprises about 2% NaCl in 1 to 2.4 mM Tris HCl, pH 8.0, preferably 2.4 mM Tris-HCl. The inclusion of EDTA in the extraction buffer appears to interfere with the action of the CTAB. It was further found that incubating plant tissue in the CTAB extraction buffer resulted in substantially most of the EPS (or LPS) being extracted from the bacteria or the plant tissue within one to two minutes.

Because the CTAB does not appear to kill the bacteria in the sample, after removing an aliquot of the CTAB extract for immunological analysis as described herein, the bacteria in the CTAB extract can be cultivated for further analysis by adding bacterial nutrient broth to the CTAB extract and incubating at the optimal temperature for growing the bacteria or plating the CTAB extract on nutrient agar.

Therefore, in the CTAB embodiment for detecting a bacterial infection in a plant, about 0.5 g of tissue from the plant is cut into pieces, added to a vial containing preferably about 0.5 mL of CTAB extraction buffer, and the mixture incubated for about one to two minutes to allow the bacteria along with EPS capsule to ooze from the tissue and the CTAB to cause the aggregation of the EPS and LPS to produce an extract of EPS and LPS. Alternatively, the tissue can be coarsely ground in the CTAB extraction buffer to release the bacteria and EPS capsule.

After the sample has been prepared using CTAB or by boiling, an aliquot (between about one to 100 μL, preferably, about 10 μL) of the extract is then transferred to a tube containing between about a 10 to 100 μL, preferably between 30 and 50 μL, volume of colored polystyrene latex particles in water at a concentration of between about 0.05% to 1%, preferably between about 0.01 and 0.15%, most preferably about 0.15%. In general, the preferred ratio of sample volume to volume of particles is about 1 to 5 for EPS and about 1 to 1 for other antigens. After about one minute, particle blocking solution containing a protein such as BSA in phosphate buffered saline containing a detergent such as polysorbate 20 (TWEEN 20), and a zwitterionic detergent such as n-dodecyl-N,N-dimethyl glycine (for example, EMPIGEN BB from Calbiochem-Novabiogen Corp., San Diego, Calif.) is added and the mixture incubated for about one minute. A preferred particle blocking solution is a 2× particle blocking solution comprising 2× phosphate buffered saline, about 4% polysorbate 20 (TWEEN 20), about 4% BSA and about 0.075% of n-dodecyl-N,N-dimethyl glycine (EMPIGEN BB), which enhances the particle flow rate and the signal-to-noise ratio. The 2× particle blocking solution is added to mixture containing the sample and polystyrene latex particles in a 1:1 ratio. After about one minute, the sample pad 20 of an immunostrip 10 prepared as described above and which comprises an antibody immobilized in the detection zone 27 which is specific for the particular EPS being assayed, is inserted into the mixture for a time sufficient to allow the mixture to flow through the sample pad 20b and the membrane 12 towards the wicking pad 24. Those polystyrene latex particles bound with EPS are captured by the antibody immobilized in the detection zone 27. Polystyrene latex particles not bound with EPS or LPS flow past the detection zone 27 towards the wicking pad 24. Because the polystyrene latex particles are colored, detection of the captured polystyrene particles bound with EPS is visually detectable as a colored line in the detection zone 27.

Optionally, the immunostrip 10 further includes a reference zone 28 comprising an antibody specific for a control antigen and the blocking solution contains colored polystyrene latex particles which have bound thereon the control antigen. The control antigen can be any antigen which does not cross-react with the antibody in the detection zone 27 or with the EPS in the sample and for which an antibody or monoclonal antibody for detecting the control antigen is available. For example, the control antigen can be mouse IgG bound or conjugated to the polystyrene latex particles and the antibody immobilized in the reference zone is goat anti-mouse IgG antibody. The mouse IgG-polystyrene latex particles are preferably provided in the particle blocking solution at a concentration of about 0.01% to 0.05%, most preferably at about 0.015%.

In the case of determining whether an animal or human host is infected with a bacteria which produces EPS and/or LPS, a fluid sample such as serum or a tissue sample is removed from the host and processed for analysis either by the boiling embodiment or the CTAB embodiment.

By using species-specific anti-EPS antibodies, the above method can also be used to detect EPS produced by fungi including, but not limited to, the various species and strains of *Accremodium, Aureobastidium* such as *A. pullulans, Aspergillus* such as *A. versicolor, Cephalosporium, Cladosporium, Exophilia, Fusarium, Paecilomyes* such as *P. Marquandii, Memnonmiella, Penicillium, Phoma, Rotorula, Stachybotrys* such as *S. chartarum* (aka atra), *Trichoderma*, yeast, ligninolytic fungi, mildew, and the like. For example, the method can be used to estimate the concentration of particular airborne fungi of importance to human health in an environment such as such as dwellings, workplaces, food processing plants, and public buildings, e.g., offices, hospitals, schools, museums, archives, and ventilation systems therein as follows. Dust samples are obtained from surfaces such as floors by using a vacuum cleaner. The samples are then sieved and the fine dust analyzed for EPS by suspending in CTAB extraction buffer and then mixing an aliquot with colored polystyrene latex particles. After blocking the particles with particle blocking solution, the mixture is analyzed on immunostrips comprising antibody specific for the EPS. In a similar manner, the above method can be used to determine the presence of fungi in soils, feedstock, foodstuffs, textiles, leathers, building materials, plants, animals, humans, and the like.

It was also discovered that the polystyrene latex particles also preferentially bind proteins produced by viruses of the potyviridae and tobamoviridae families over other proteins which might be present in an extract prepared from plant tissue. Potyviridae are non-enveloped, single-stranded RNA viruses comprising the species Potyvirus, Rymovirus, and Bymovirus. The following viruses are members of the potyviridae family and can be detected using the method of the present invention: Alstroemeria mosaic potyvirus, Amaranthus leaf mottle potyvirus, Araujia mosaic potyvirus, Arracacha Y potyvirus, Artichoke latent potyvirus, Asparagus 1 potyvirus, Banana bract mosaic potyvirus, Bean common mosaic necrosis potyvirus, Bean common mosaic potyvirus, Bean yellow mosaic potyvirus, Beet mosaic potyvirus, Bidens mosaic potyvirus, Bidens mottle potyvirus, Cardamom mosaic potyvirus, Carnation vein mottle potyvirus, Carrot thin leaf potyvirus, Cassava brown streak potyvirus, Cassia yellow spot potyvirus, Celery mosaic potyvirus, Chickpea bushy dwarf potyvirus, Chickpea distortion mosaic potyvirus, Clover yellow vein potyvirus, Commelina diffusa potyvirus, Commelina mosaic potyvirus, Cowpea green vein-banding potyvirus, Cowpea Moroccan aphid-borne mosaic potyvirus, Cowpea rugose mosaic potyvirus, Crinum mosaic potyvirus, Daphne Y potyvirus, Dasheen mosaic potyvirus, Datura Colombian potyvirus, Datura distortion mosaic potyvirus, Datura necrosis potyvirus, Datura shoestring potyvirus, Dendrobium mosaic potyvirus, Desmodium mosaic potyvirus, Dioscorea alata potyvirus, Dioscorea green banding mosaic potyvirus, Eggplant green mosaic potyvirus, Euphorbia ringspot potyvirus, Freesia mosaic potyvirus, Groundnut eyespot potyvirus, Guar symptomless potyvirus, Guinea grass mosaic potyvirus, Helenium Y potyvirus, Henbane mosaic potyvirus, Hippeastrum mosaic potyvirus, Hyacinth mosaic potyvirus, Iris fulva mosaic potyvirus, Iris mild mosaic potyvirus, Iris severe mosaic potyvirus, Johnsongrass mosaic potyvirus, Kennedya Y potyvirus, Leek yellow stripe potyvirus, Lettuce mosaic potyvirus, Lily mottle potyvirus, Maize dwarf mosaic potyvirus, Malva vein clearing potyvirus, Marigold mottle potyvirus, Narcissus yellow stripe potyvirus, Nerine potyvirus, Onion yellow dwarf potyvirus, Ornithogalum mosaic potyvirus, Papaya ringspot potyvirus, Parsnip mosaic potyvirus, Passiflora ringspot potyvirus, Passiflora South African potyvirus, Passionfruit woodiness potyvirus, Patchouli mosaic potyvirus, Pea mosaic potyvirus, Pea seed-borne mosaic potyvirus, Peanut green mosaic potyvirus, Peanut mottle potyvirus, Pepper Indian mottle potyvirus, Pepper mottle potyvirus, Pepper severe mosaic potyvirus, Pepper veinal mottle potyvirus, Plum pox potyvirus, Pokeweed mosaic potyvirus, Potato A potyvirus, Potato V potyvirus, Potato Y potyvirus, Primula mosaic potyvirus, Ranunculus mottle potyvirus, Sorghum mosaic potyvirus, Soybean mosaic potyvirus, Statice Y potyvirus, Sugarcane mosaic potyvirus, Sweet potato feathery mottle potyvirus, Sweet potato G potyvirus, Swordbean distortion mosaic potyvirus, Tamarillo mosaic potyvirus, Telfairia mosaic potyvirus, Tobacco etch potyvirus, Tobacco vein-banding mosaic potyvirus, Tobacco vein mottling potyvirus, Tobacco wilt potyvirus, Tomato Peru potyvirus, Tradescantia-Zebrina potyvirus, Tropaeolum 1 potyvirus, Tropaeolum 2 potyvirus, Tuberose potyvirus, Tulip band-breaking potyvirus, Tulip breaking potyvirus, Tulip chlorotic blotch potyvirus, Turnip mosaic potyvirus, Ullucus mosaic potyvirus, Vallota mosaic potyvirus, Vanilla mosaic potyvirus, Vanilla necrosis potyvirus, Voandzeia distortion mosaic potyvirus, Watermelon mosaic 1 potyvirus, Watermelon mosaic 2 potyvirus, Wild potato mosaic potyvirus, Wisteria vein mosaic potyvirus, Yam mosaic potyvirus, Zucchini yellow fleck potyvirus, and Zucchini yellow mosaic potyvirus.

Tentative viruses of the potyviridae family include Asystasia gangetica mottle potyvirus, Celery latent potyvirus, Datura mosaic potyvirus, Endive necrotic mosaic potyvirus, Kalanchoe mosaic potyvirus, Konjak mosaic potyvirus, Nasturtium mosaic potyvirus, Patchouli mottle potyvirus, Shallot yellow stripe potyvirus, Sweet potato vein mosaic potyvirus, and Welsh onion yellow stripe potyvirus.

Tobamoviridae are single-stranded RNA viruses which include viruses such as Cucumber green mottle mosaic tobamovirus, Frangipani mosaic tobamovirus, Kyuri green mottle mosaic tobamovirus, Odontoglossum ringspot tobamovirus, Paprika mild mottle tobamovirus, Pepper mild mottle tobamovirus, Ribgrass mosaic tobamovirus, Opuntia Sammons' tobamovirus, Sunn-hemp mosaic tobamovirus, Tobacco mild green mosaic tobamovirus, Tobacco mosaic tobamovirus, Tomato mosaic tobamovirus, and Ullucus mild mottle tobamovirus. The following viruses have been tentatively assigned to the tobamoviridae family Hibiscus yellow mosaic tobamovirus, Maracuja mosaic tobamovirus, Potato 14R tobamovirus, and Rose tobamovirus.

The general method for detecting a virus or proteins thereof of the potyviridae or tobamoviridae group is as follows. A sample from an organism suspected of being infected with the virus is provided as a liquid extract. For example, in the case of testing a plant tissue for infection by the virus, the tissue is ground in an aqueous buffer solution such as a carbonate-bicarbonate buffer at a pH of about 9.0 to 9.6 at a ratio of about 1 gram to 10 grams buffer to elute the virus.

After the sample has been prepared, an aliquot (between about one to 100 µL, preferably, about 25 to 50 µL) of the extract is then transferred to a tube containing between about a 10 to 100 µL, preferably between 30 and 50 µL, volume of colored polystyrene latex particles in water at a concentration of between about 0.05% to 1%, preferably between about 0.01 and 0.15%, most preferably about 0.15%. In general, the preferred ratio of sample volume to volume of particles is about 1 to 1. After about 10 to 30 minutes, preferably 10 minutes, particle blocking solution containing a protein such as BSA in phosphate buffered saline containing a detergent such as polysorbate 20 (TWEEN 20), and a zwitterionic detergent such as n-dodecyl-N,N-dimethyl glycine is added and the mixture incubated for about one minute. A preferred particle blocking solution is a 2× particle blocking solution comprising 2× phosphate buffered saline, about 4% polysorbate 20 (TWEEN 20), about 4% BSA and about 0.075% of n-dodecyl-N,N-dimethyl glycine. The 2× particle blocking solution is added to mixture containing the sample and polystyrene latex particles in a 1:1 ratio. After about one minute, the sample pad 20 of an immunostrip 10 prepared as described above and which comprises an antibody immobilized in the detection zone 27 which is specific for the particular virus being assayed, is inserted into the mixture for a time sufficient to allow the mixture to flow through the sample pad 20b and the membrane 12 towards the wicking pad 24. Those polystyrene latex particles bound with virus or proteins thereof are captured by the antibody immobilized in the detection zone 27. Polystyrene latex particles not bound with virus or proteins thereof flow past the detection zone 27 towards the wicking pad 24. Because the polystyrene latex particles are colored, detection of the captured polystyrene particles bound with virus or proteins thereof is visually detectable as a colored line in the detection zone 27. Optionally, the immunostrip 10 further includes a reference zone 28 comprising an antibody specific for a control antigen and the blocking solution contains colored polystyrene latex particles which have bound thereon the control antigen as described previously.

The immunoassay of the present invention is not limited to detecting EPS and/or LPS or the above mentioned virus proteins. The immunoassay can also be used to detect particular antibody molecules. For example, the method can be used to determine whether a sample such as serum from an animal or human contains a particular antibody by adsorbing the antibodies in the serum to the polystyrene latex particles and blocking as described above and then applying to an immunostrip described as above but wherein the detection zone comprises an analyte which is specifically bound by the antibody which is the object of the immunoassay to capture the antibody in the serum which is specific for the analyte.

The immunoassay of the present invention is useful for detecting diseases of human or veterinary importance caused by viruses, bacteria, fungi, parasites, and the like. For example, immunoassays for detecting diseases of human importance include, but are not limited to, immunoassays for detecting antigens of or antibodies against toxosidiois, rubella, CVM, herpes simplex virus (1 or 2), *Chlamydia, H. pylori, Syphilis, Brucella,* tuberculosis, measles, mumps, VZV, influenza, parainfluenza, adenovirus, leptospira, HTLV, Epstein Barr virus, respiratory syncytial virus, VLA, varicella, streptococcus, mononucleosis, malaria, hepatitis, typhoid, *Echinococcus, Cysticerosis,* amoebiasis, *Candida, E. coli* O157, *E. coli* verotoxin, rotavirus, staphylococcus, and meningitis. Immunoassays for detecting other human diseases of importance include, but are not limited to, assays for detecting various cancer antigens such as alpha-feto protein, carcinoembryonic antigen, prostrate specific antigens, human chorionic gonadotropin, and the like. Diseases of veterinary importance include, but are not limited to, assays for detecting particular antigens of or particular antibodies against feline leukemia virus, feline herpesvirus, leishmania, heart worm, canine parvovirus, hog cholera, pseudorabies, parainfluenza virus, porcine reproductive and respiratory syndrom virus, porcine influenza, *Eryspelothix rhusiopathic,* bovine respiratory syncytial virus, bovine viral diarrhea virus, adenovirus 3, *Faciola hepatica,* rotavirus, coronavirus, Cryptosporidium, bovine herpesvirus, viral haemorrhagic septicaemia, infectious haematopoietic necrosis, infections pancreatic necrosis, spring viraema of carp, *Chlamydia psittaci, Mycoplasma agalactiae,* infectious laryngotracheitis virus, turkey rhinotracheitis, and Marek's disease virus.

The immunoassay of the present invention can also be used for detecting cytokines; assays for detecting cardiac markers such as myoglobin, troponins, and the like; assays for detecting autoimmune markers such as anti-nuclear antibody (ANA), anti-double-stranded DNA antibody, anti-SmRNA antibody, rheumatoid factor, and the like; assays for detecting various drugs in a test subject such as cotinine, opiates, and the like; and, assays for determining thyroid, hormone, and fertility profiles of a patient.

The immunoassay of the present invention can be used to detect recombinant proteins produced by a transgenic organism or plant. For example, Bt-Cry1Ab protein and Bt-Cry1Ac protein, which are expressed in transgenic crops such as cotton and corn varieties; Bt-Cry3A protein, which is produced in transgenic potato plants; Bt-Cry9C endotoxin, which is produced in some varieties of transgenic corn; and, neomycin phosphotransferase II (NPTII), a common marker used for making transgenic plants.

The immunoassay of the present invention can be conveniently provided as a kit. The preferred kit comprises the following components: (1) a detection apparatus as described above and shown in FIGS. 1a and 1b, (2) a first container containing extraction solution for extraction of an analyte such as EPS or LPS or virus proteins, preferably, in the case of a kit for detecting EPS or LPS, the extraction solution comprises CTAB (3) a second container containing a particle blocking solution, which optionally further comprises control particles; and (4) a third container containing a suspension comprising colored particles which are capable of binding of an analyte such as EPS or LPS or virus proteins, preferably the colored polystyrene latex particles described above. Preferably, the suspension of colored particles and the particle blocking solution are provided in dropper bottles. Preferably, the dispensing end of the spout of the dropper bottle has a diameter sufficient to dispense drops with a volume between 30 and 60 µL.

The immunoassay of the present invention can also be used for rapid screening a library of monoclonal antibody clones for those clones in the library which produce antibodies (IgG, IgM, IgA, IgE) against a particular analyte (antigen) or epitope thereof. It is known in the art that monoclonal antibodies which might be useful for binding an analyte in an ELISA format might not be useful for binding an analyte in immunostrip format. The method herein enables the behavior of particular monoclonal antibodies in an immunostrip format to be ascertained. Thus, the method is particularly useful for identifying those monoclonal antibodies which are particularly useful for immunostrip assays.

The method uses the above particles bound with the analyte or particular epitope thereof and an immunostrip which has immobilized in the detection zone an antibody which is specific for the species of monoclonal antibody comprising the library. For example, when the library of monoclonal antibodies is produced using mouse hybridomas, the immunostrip comprises anti-mouse antibodies immobilized in the detection zone to bind those mouse monoclonal antibodies which are specific for the analyte or particular epitope thereof.

In general, the rapid screening method is performed as follows. A solution of the analyte or particular epitope thereof is mixed with the above particles for a time sufficient to allow the analyte to be adsorbed to the particles. Preferably, after the analyte is bound to the particles, the particles are blocked with a blocking agent such as bovine serum albumin to ensure that any sites on the particles not bound to the analyte are blocked. A suitable blocking solution can include the particle blocking solution previously described.

Next, one or more microtiter plates comprising for each well, an aliquot of a monoclonal antibody clone from the library. Then, for each well, an aliquot of the particles bound with analyte is then added. The antibodies produced by those clones which are specific for the analyte bind the analyte bound to the particles to form antibody-analyte complexes bound to the particles. In particular embodiments, the immunostrip can further include a reference zone prepared as above and an aliquot of particles comprising a control analyte is added to the well with the particles bound to the analyte.

Finally, for each well, the sample pad of an immunostrip with an antibody specific for the species of antibody produced by the library is immersed in the well. For those wells containing an antibody specific for the analyte or particular epitope thereof, the particles bound to the antibody-analyte complex are captured by the antibody immobilized in the detection zone. In this manner, in single assay, a plurality of monoclonal antibody clones can be rapidly screened for those clones which produce antibodies against the analyte or particular epitopes thereof.

In general, monoclonal antibodies are of mouse origin; however, the monoclonal antibody as used herein also refers to any clonal population of an antibody made against a particular epitope of an analyte produced by phage display technology or a method that is equivalent to phage display or hybrid cells of non-mouse origin. The term further includes methods for humanizing antibodies. These methods are well known in the art.

The above method can be provided as a kit comprising immunostrips prepared as previously described above in which antibodies specific for the species antibody produced by the library are immobilized in the detection zone. For example, for use with mouse-derived monoclonal antibody libraries, the detection zone comprises an anti-mouse antibody (for example goat anti-mouse IgG antibody). Optionally, the immunostrip can include a reference zone and the kit include particles with a reagent bound thereon which is captured by a binding member for the reagent immobilized in the reference zone. For example, the reference zone can comprise anti-equine antibodies and the control particles can comprise equine IgG. The kit can further include particles, preferably as a suspension in water, in a container for the user of the kit to bind to an analyte or epitope thereof for screening the monoclonal library, a container containing a solution for preparing an analyte for adsorption to the particles, and a container containing a particle blocking solution such as those described above. Optionally, the kit can further comprise solutions for mixing with the aliquots obtained from the library.

Thus, the immunoassay of the present invention can be used for immunoassays for detecting an analyte which is selected from the group consisting of protein, polysaccharide, and chemical, particularly, wherein the protein is selected from the group consisting of viral protein, bacterial protein, immunoglobulin, parasite protein, plant protein, mammalian protein, hormone, and insect protein; the polysaccharide is selected from the group consisting of extracellular polysaccharides (EPS) and lipopolysaccharides (LPS); and, the chemical is an organic compound selected from the group consisting of herbicide, pesticide, drug, nutraceutical, and derivative thereof. The important elements of the immunoassay include that the analyte have the ability to bind to the polystyrene latex particles and that a binding member specific for the analyte, preferably an antibody, can be immobilized in the detection zone on the immunostrip for binding the analyte.

The following examples are intended to promote a further understanding of the present invention.

EXAMPLE 1

This example illustrates the process for developing the lateral flow immunochromatography method of the present invention for detecting in a sample from a plant EPS or LPS produced by a particular bacteria.

Colored polystyrene particles (latex) of different diameters were evaluated for their lateral flow characteristics on nitrocellulose membranes of different pore sizes. Colored polystyrene latex particles with diameters of 0.06 µm, 0.25 µm, and 0.77 µm and dyed blue were obtained from Bangs Laboratories, Inc., Fishers, Ind. The nitrocellulose membranes which were tested had pore sizes of 15 µm (HF 75 from Millipore Corp., Bedford, Mass.), 12 µm (AE 100 from Schleicher and Schuell, Keene, N.H.), 10 µm (CN 140 from Sartorius, Edgewood, N.Y.), and 12 µm (Predator from Pall Corporation, East Hills, N.Y.). Colored polystyrene latex particles of each diameter were each suspended at 1:10, 1:100, and 1:1000 dilutions in water. For each dilution, one end of each of the nitrocellulose membranes with a pore size of 10 µm, 12 µm, and 15 µm on a polymer coated card stock support member and a wicking pad in lateral contact with the opposite end was submerged into the suspension of particles. The lateral flow of particles to the wicking pad at room temperature was monitored.

Figure 2:
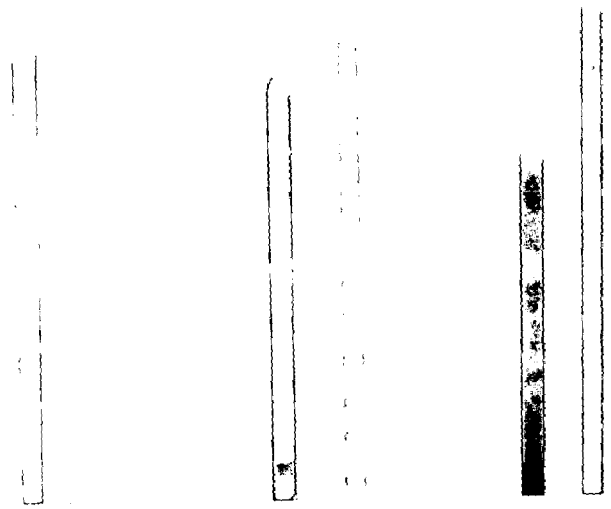
FIG. 2 shows the lateral flow characteristics of colored polystyrene latex particles on a 15 µm Millipore HF 75 nitrocellulose membrane. Lanes 1 to 3 show the flow characteristics of particles with a diameter of 0.06 µm at 1:10 (lane 1), 1:100 (lane 2), and 1:1000 (lane 3) dilutions. Lanes 4 to 6 show the flow characteristics of particles with a diameter of 0.25 µm at 1:10 (lane 4), 1:100 (lane 5), and 1:1000 (lane 6) dilutions in water. Lanes 7 to 9 show the flow characteristics of particles with a diameter of 0.77 µm at 1:10 (lane 7), 1:100 (lane 8), and 1:1000 (lane 9) dilutions in water on a 15 µm Millipore HF 75 nitrocellulose membrane.

FIG. 2 shows the lateral flow characteristics of 0.06 µm diameter particles at 1:10 (lane 1), 1:100 (lane 2), and 1:1000 (lane 3) dilutions on a Millipore HF 75 nitrocellulose membrane with a 15 µm pore size, the lateral flow characteristics of 0.25 µm diameter particles at 1:10 (lane 4), 1:100 (lane 5), and 1:1000 (lane 6) dilutions on a Millipore HF 75 nitrocellulose membrane with a 15 µm pore size, and the lateral flow characteristics of 0.77 µm diameter particles at 1:10 (lane 7), 1:100 (lane 8), and 1:1000 (lane 9) dilutions on a Millipore HF 75 nitrocellulose membrane with a 15 µm pore size. Under the above conditions, the particles with a 0.77 µm diameter and at a 1:1000 dilution (0.1%) had desirable lateral flow characteristics.

Figure 3:
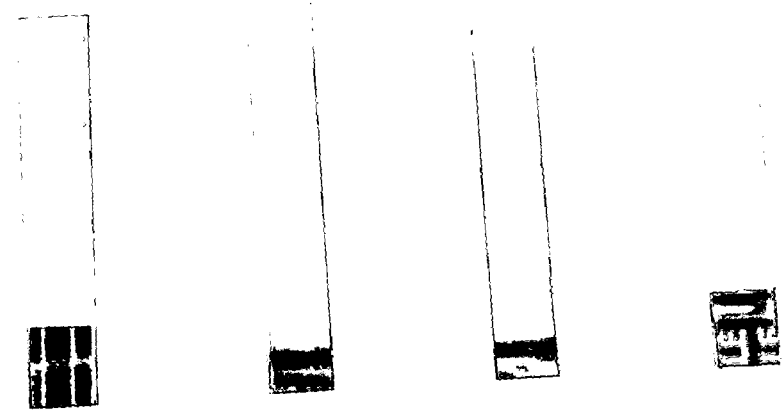
FIG. 3 shows the lateral flow characteristics of colored polystyrene latex particles with a diameter of 0.77 µm at a 0.05% dilution in water on a Millipore HF 75 15 µm nitrocellulose membrane (lane 1), a Schleicher and Schuell AE100 12 µm nitrocellulose membrane (lane 2), a Sartorius CN 140 10 µm nitrocellulose membrane (lane 3), and a Pall PREDATOR 12 µm nitrocellulose membrane (lane 4).

FIG. 3, lane 1, shows that the lateral flow characteristics of the colored polystyrene latex particles at a concentration of 0.05% in water with a 0.77 µm diameter on the 15 µm Millipore HF 75 membrane had the most desirable lateral flow characteristics compared to the 12 µm AE100 (lane 2), 10 µm CN 140 (lane 3), and 12 µm Predator (lane 4) membranes. While membranes with pore sizes greater than 15 µm enabled the particles to flow through the membrane relatively unhindered, the ability of the membrane to bind antibody at the detection zone appeared to be reduced. Particles with a diameter less than 0.77 µm appeared not to have good flow characteristics regardless of whether the pore size of the membrane was 12 µm or 15 µm. The results indicate that lateral flow of the particles through a particular membrane is related to the ratio of the pore size of the membrane to the diameter of the particles. In this set of experiments, a 15 μm nitrocellulose membrane and 0.77 μm particles were found to be a good combination.

To test the above combination of 0.77 μm particles with 15 μm nitrocellulose membranes in a lateral flow immunochromatography assay for detecting EPS, EPS was extracted from *Ralstonia solanacerarum* (Rs) infected plant tissue as follows. Rs infected tissue was suspended in a TBSE buffer (2 mM Tris-HCl, pH 9.2, 2% NaCl, and 0.01% EDTA) and boiled for 10 minutes to disrupt the bacteria and extract the EPS. Afterwards, 5 μL of the boiled suspension was mixed with 5 μL of the above 0.77 μm colored polystyrene latex particles (0.05% in water) and 90 μL of carbonate-bicarbonate buffer, pH 9.0, for 10 minutes at room temperature. Afterwards, sites on the particles not bound by the EPS were blocked by adding a solution containing 0.5% bovine serum albumin (BSA) in the carbonate-bicarbonate buffer for five minutes at room temperature.

Next, the sample application end of an immunostrip was submerged into the above suspension for 10 minutes at room temperature. The immunostrip comprised a 15 μm HF 75 membrane on a polymer coated card stock. The end opposite to the sample application end was in lateral contact with a wicking pad. In a detection zone at a position laterally spaced from the sample application end, anti-Rs monoclonal antibody (ascites fluid) at a 1:10 dilution was striped and then immobilized by drying at 37° C. overnight. A control prepared from uninfected plant tissue as above was run in parallel.

Figure 4A:
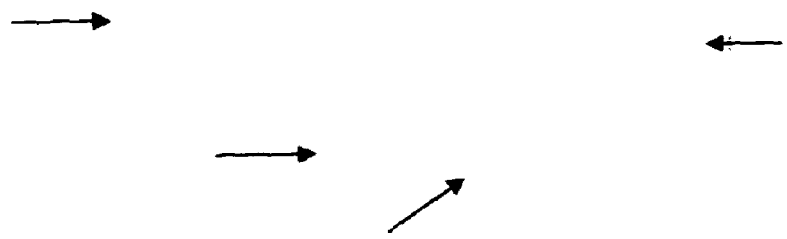
FIG. 4a shows the results of an immunoassay for detecting EPS produced by *Ralstonia solanacerarum* (Rs) using 0.77 µm colored polystyrene latex particles and an immunostrip comprising a 15 µm nitrocellulose membrane and anti-Rs monoclonal antibody in the detection zone wherein the extraction and immunoassay were performed using
Figure 4B:
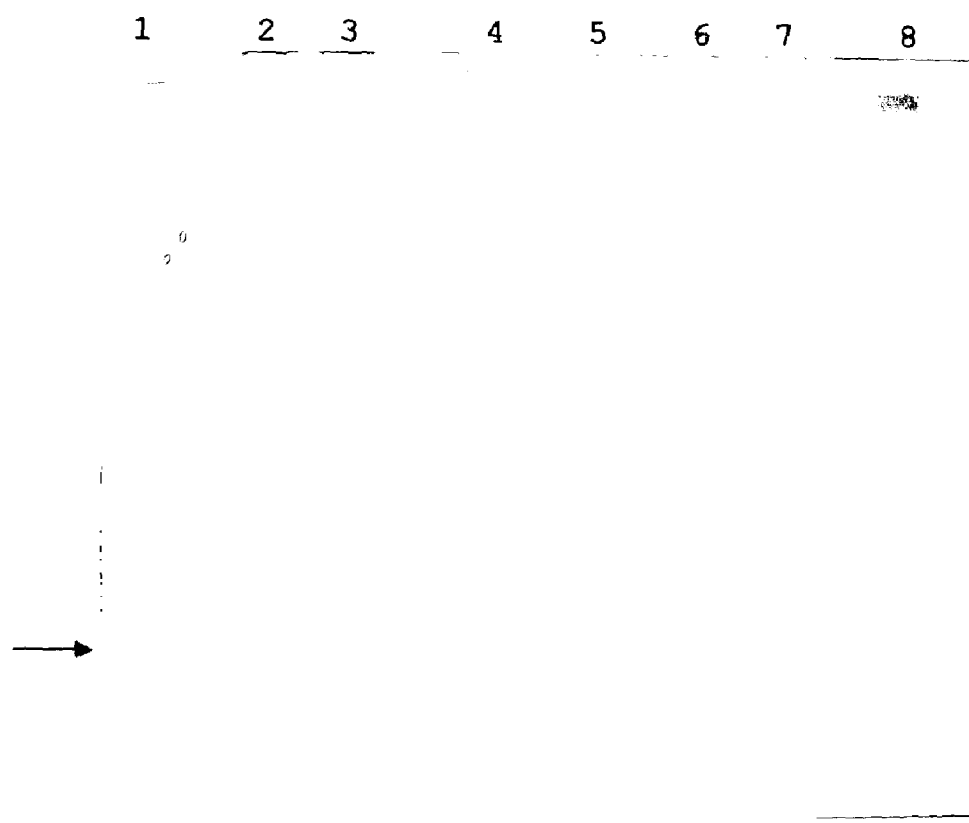
Figure 4C:
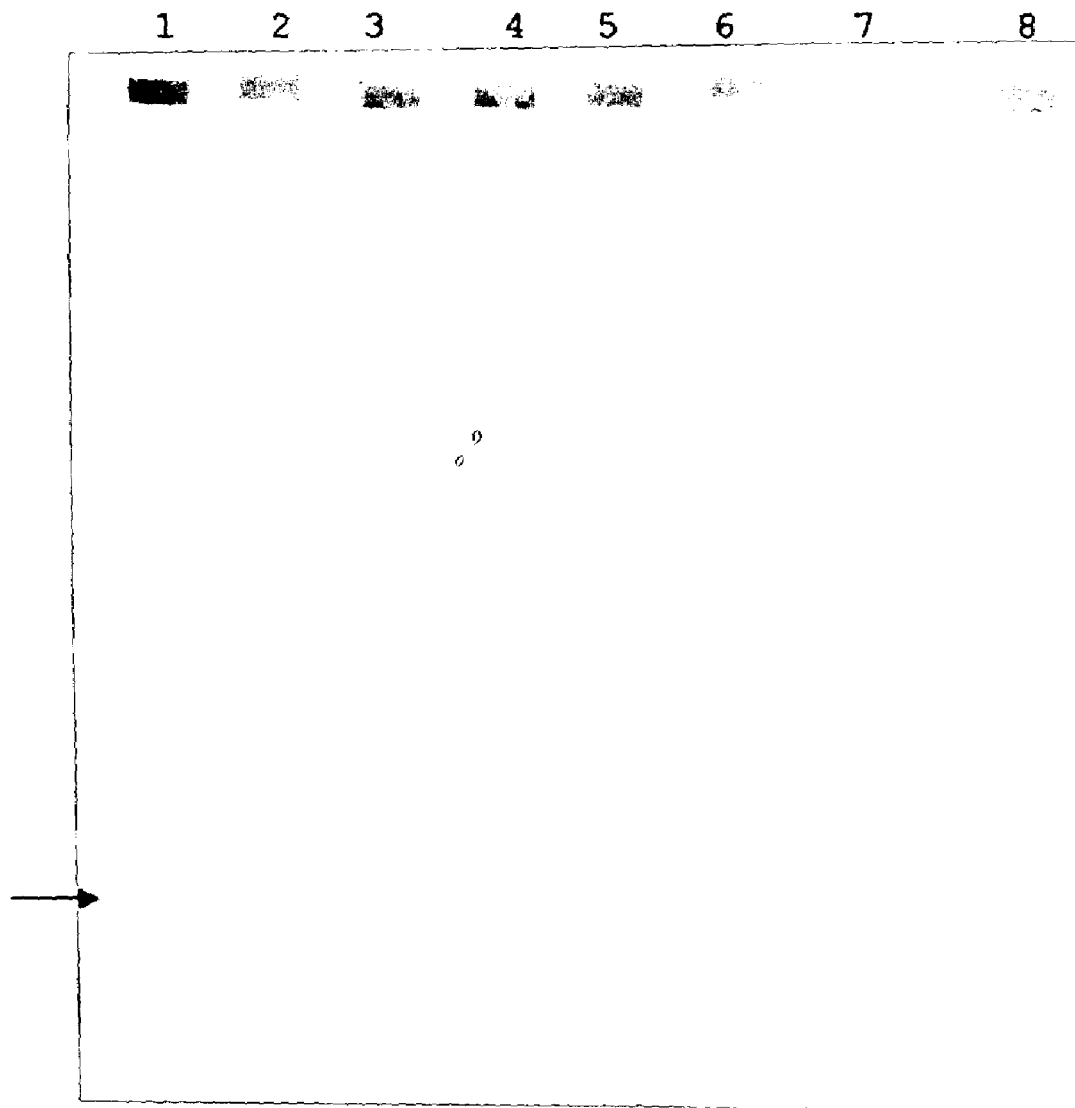
Figure 4D:
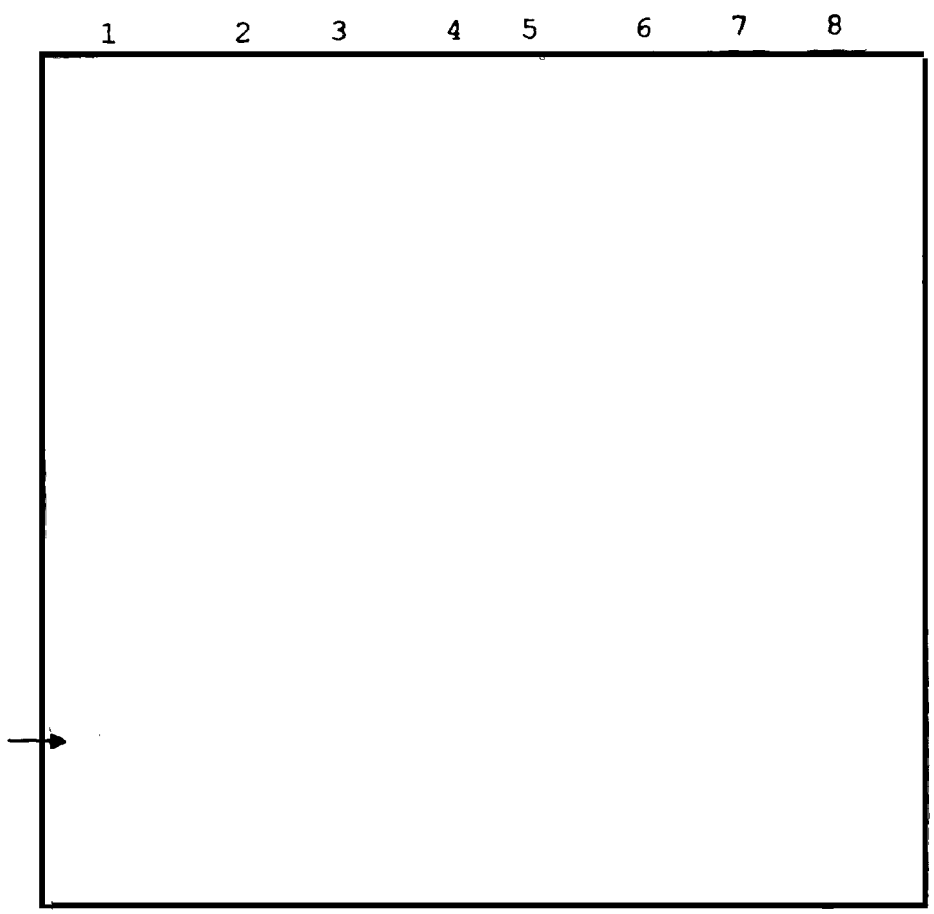
Figure 4E:
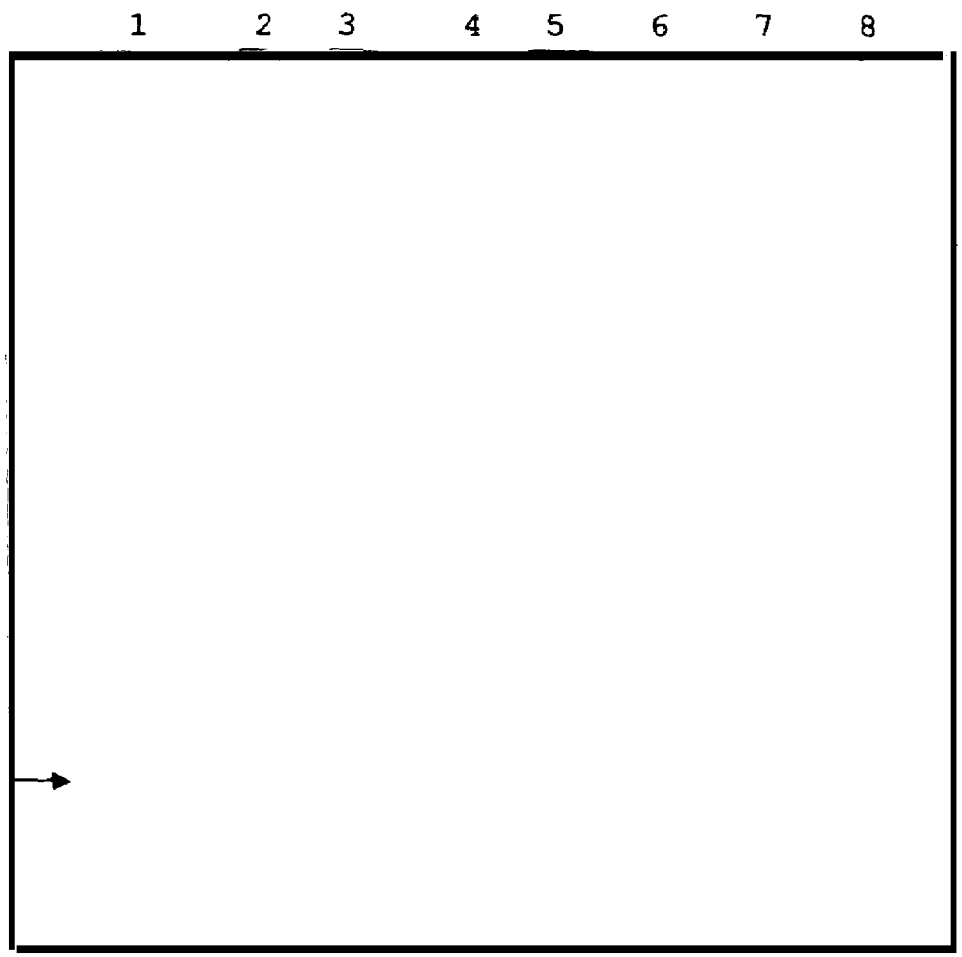

The results shown in FIG. 4a showed that a specific signal was obtained in the detection zone (lanes 1 and 4); however, in this experiment, aggregation of the particles was noticed with the negative controls which might have been caused by the high pH of the carbonate buffer, insufficient blocking of the particles (lanes 2 and 3). In addition, as shown in FIGS. 4b to 4e, cross-reactivity with non-Rs EPS (EPS from other pathogenic and non-pathogenic bacteria) was also observed which might have been caused by insufficient blocking of the particles which might have enabled the particles to adsorb to the immobilized antibody. That is, unbound sites on the particles were available to bind by adsorption to the immobilized anti-Rs antibody in the detection zone.

The specificity of the immunoassay for Rs EPS without substantial cross-reactivity with non-Rs EPS was achieved by increasing the BSA concentration in the particle blocking solution to 2.0% and using phosphate buffered saline containing 2.0% Tween-20 (PEB) instead of the carbonate-bicarbonate buffer. Reagents such as Triton X-100, polyethylene glycol (PEG), or EMPIGEN BB did not appear to affect specificity.

After several experiments, preferred conditions for the immunoassay were found to include at the following ratios 25 μL of 0.10 to 15% particles in water, 3 μL of sample solution containing EPS prepared as above, 25 μL of 2% BSA in water, and 6 μL of PEB buffer. The incubation times for each of the above steps were also reduced to five minutes boiling, two minutes incubation with the particles, and two minutes blocking with BSA. Under the above conditions, the immunoassay was specific for Rs EPS without detectable cross-reactivity with EPS from other pathogenic or non-pathogenic bacteria.

Thus, in a typical reaction a sample containing EPS is prepared by boiling 5 minutes as above. Then a 3 μL aliquot of the sample is mixed with 25 μL of a 0.10 to 15% suspension of 0.77 μm particles in water and incubated for two minutes at room temperature. Afterwards, 25 μL of 2% BSA in water and 6 μL of PEB buffer is added and the mixture is incubated for 2 minutes at room temperature. Finally, the sample application end of an immunostrip comprising a 15 μm pore membrane and antibody striped in a detection zone is immersed in the mixture and the immunostrip developed for about 10 minutes at room temperature.

EXAMPLE 2

The next objective was to use the information in Example 1 to develop a more user friendly format for delivery of the reagents to the immunostrip. Three different approaches were used: (1) drying the colored polystyrene latex particles into a sample pad which is then incorporated into the immunostrip, (2) consolidating the different liquid components to enable the method to be performed in three steps, that is, (a) add sample to colored polystyrene latex particles, (b) then add particle blocking solution to sample and particles, and (c) then immerse end of immunostrip into the mixture of step (b), and (3) using a standard dropper bottle for delivery of the colored polystyrene latex particles and particle blocking solution.

Figures 5A, 5B:

In the first approach, the colored polystyrene latex particles were incorporated into the sample pad and dried. In this embodiment, the sample is applied to the sample pad wherein the EPS then binds the colored polystyrene latex particles which then migrate to the detection zone. Different concentrations of colored polystyrene particles in either water or phosphate buffered saline, with or without mannitol, were soaked onto polyester pads (16-S, Schleicher and Schuell) or glass fiber filter pads (GFCP203000, Millipore Corporation). The pads were then air dried at ambient temperature or at 37° C. or lyophilized. Regardless of which of the above methods was used, many of the particles did not elute properly from the pads during chromatography as described above and of those particles which did elute many did not appear to bind the EPS (FIG. 5a). The particles were also coated to the bottom of a glass tube by either lyophilization, air drying, or drying at 37° C. When the particles were reconstituted in water or buffer for the above assay, the signal at the detection zone was reduced several fold (FIG. 5b).

In the second approach, several of the liquid components of the assay were combined into three elements: a 0.10 to 0.15% solution of the colored polystyrene latex particles in water, a solution of the sample as above, and a particle blocking solution (2% BSA in phosphate buffered saline containing 2% polysorbate 20 (TWEEN 20).

Figure 6:
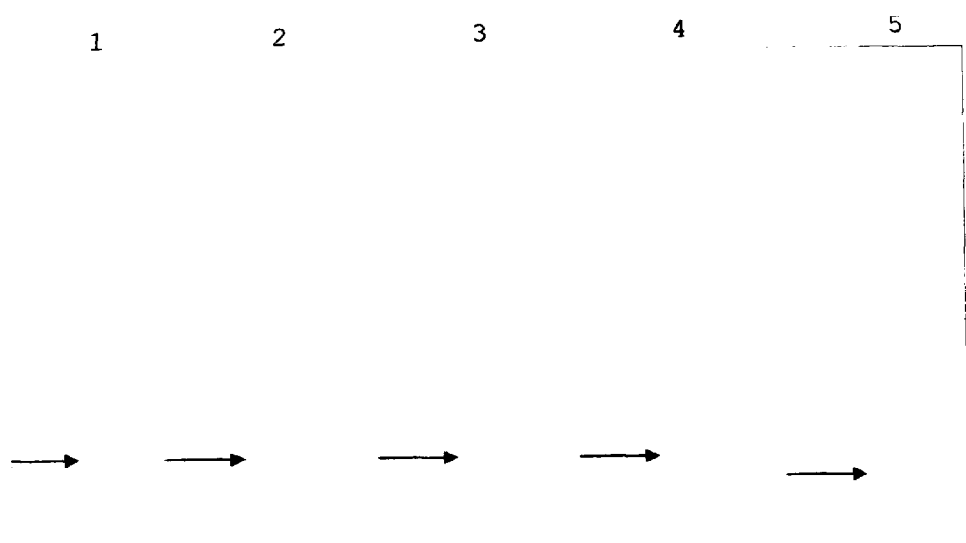

Thus, in a typical reaction a sample containing EPS is prepared by boiling 5 minutes as above. Then a 3 μL aliquot of the sample is mixed with 25 μL of a 0.10 to 0.15% suspension of 0.77 μm particles in water and incubated for two minutes at room temperature. Afterwards, 25 μL of 2% BSA in PEB buffer is added and the mixture incubated for 2 minutes at room temperature. Finally, the sample application end of an immunostrip comprising a 15 μm pore membrane and antibody striped in a detection zone is immersed in the mixture and the immunostrip developed for about 10 minutes at room temperature. It was also found that sensitivity of the immunoassay did not decrease when the steps of the immunoassay was reduced to 5 minutes boiling, 1 minute incubation with particles at room temperature, and 1 minute incubation with blocking solution at room temperature as shown in FIG. 6 which shows that the sensitivity using 1 minute incubation times appeared to be equivalent to the sensitivity using 5 minute incubation times.

With respect to the third approach, it was found that delivery of the colored polystyrene latex particles and the particle blocking solution could each be conveniently achieved by using a dropper bottle format to dispense 40 to 50 μL aliquots (drops) of each. The dropper bottles which were used were 15 mL Boston round dropper bottles comprising low density polyethylene (LDPE 5104) with polypropylene (PP) covers and dispensing spouts (Wheaton Science Products, Millville, N.J., Cat. No. 20641-037). The bottle spout openings were about 1 mm.

The results of the second and third approaches indicated that the immunoassay in a kit format can comprise immunostrips for detecting particular EPS or LPS producing microorganisms, a dropper bottle containing a 0.10 to 0.15% suspension of the 0.77 μm colored polystyrene latex particles, and a dropper bottle containing the particle blocking solution. Optionally, the kit can further contain a solution for preparing sample extracts comprising EPS or LPS.

EXAMPLE 3

The signal-to-noise ratio of the capture monoclonal antibody immobilized at the detection zone was improved by partially purifying the monoclonal antibody by ammonium sulfate precipitation. The preferred concentration of antibody for immobilizing at the detection zone was found to be about 1 mg/mL.

Figure 7:
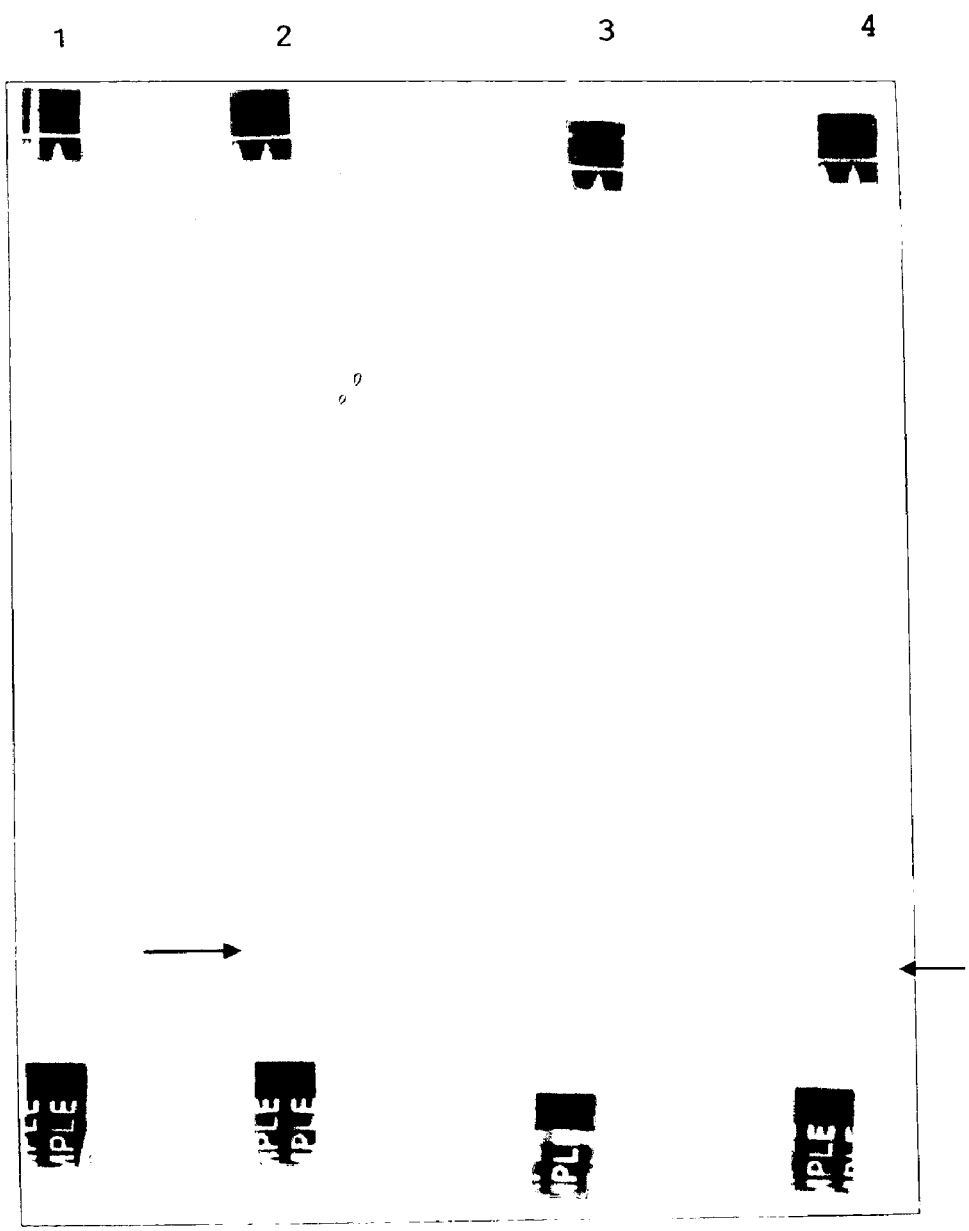
FIG. 7 shows that pretreating the 15 µm nitrocellulose membrane of the immunostrip with 2% BSA in PBS and then drying before use enhanced the lateral flow of the 0.77 µm colored polystyrene latex particles. Lanes 1 and 2 show the results of immunoassays for detecting Rs EPS wherein the membrane was untreated and lanes 3 and 4 show the results of immunoassays for detecting Rs EPS wherein the membrane had been pretreated with 2% BSA in PBS and dried before use. Lanes 1 and 3 are negative controls. Arrows point to captured EPS-bound particles in the detection zone.

The flow of the sample and colored polystyrene latex particles through the membrane was enhanced by first blocking the membrane with a membrane blocking solution containing 2% BSA in PBS and drying at 37° C. for one to two hours after the antibody had been bound to the membrane. Blocking the membrane gave a clean appearance to the immunostrip after the immunoassay because most of the particles appeared either to have been bound by the antibody at the detection zone (when the particles were bound to EPS) or to have flowed into the wicking pad (when the particles were not bound to EPS) as shown in FIG. 7 which compares the results obtained with unblocked immunostrips (lanes 1 and 2) with the results obtained with immunostrips blocked as above (lanes 3 and 4).

Figure 8:
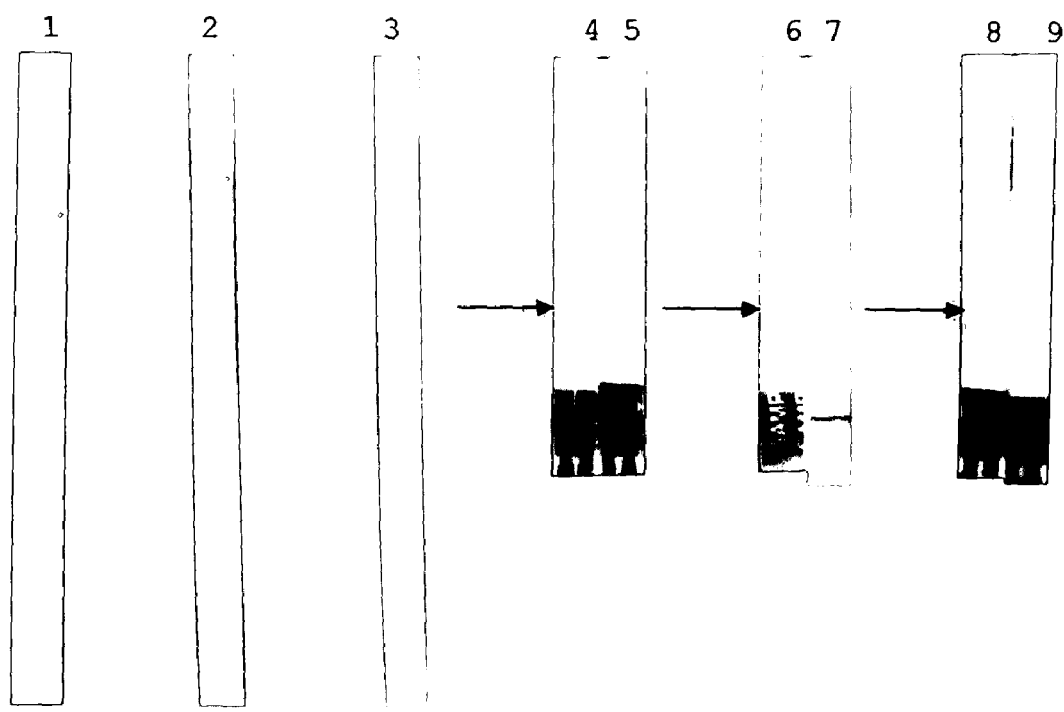
FIG. 8 shows that sample pads comprising glass fibers is preferred over sample pads comprising filter paper or polyester and that pretreating the sample pad with particle blocking solution and then drying before using the sample pad enhances the lateral flow of the 0.77 µm colored polystyrene latex particles on the immunostrip. Lane 1 show the results of an immunoassay for detecting Rs EPS wherein the sample pad comprised filter paper which had been pretreated with SEB1 solution. Lane 2 show the results of an immunoassay for detecting Rs EPS wherein the sample pad comprised filter paper which had been pretreated with SEB2 solution. Lane 3 show the results of an immunoassay for detecting Rs EPS wherein the sample pad comprised filter paper which had been pretreated with SEB3 solution. Lane 4 show the results of an immunoassay for detecting Rs EPS wherein the sample pad comprised glass fiber which had been pretreated with SEB2 solution and lane 5 is a negative control of the same. Lane 6 show the results of an immunoassay for detecting Rs EPS wherein the sample pad comprised glass fiber which was untreated and lane 7 is a negative control of the same. Lane 8 show the results of an immunoassay for detecting Rs EPS wherein the sample pad comprised a glass fiber which had been pretreated with particle blocking solution and lane 9 is a negative control of the same. Arrows point out EPS-bound particles captured in the detection zone.

Filter paper, polyester, and glass fiber pads treated with SEB1, SEB2, SEB3, polyoxyethylenesorbitan monolaurate (polysorbate 20 or TWEEN 20, a trademark of Atlas Chemical Co.), gelatin (PRIONEX, a trademark of Pentapharm Ltd., Basel, Suisse), or the particle blocking solution were each tested for use in the immunoassay. SEB1, SEB2, and SEB3 are proprietary solutions available from Agdia, Elkhart, Ind. FIG. 8 shows the results using filter paper treated with SEB1 (lane 1), filter paper treated with SEB2 (lane 2), filter paper treated with SEB3 (lane 3), glass fiber pad treated with SEB2 (lane 4), glass fiber pad untreated (lane 5 (EPS) and lane 6 (negative control), and glass fiber pad treated with particle blocking solution (lane 8 (EPS) and lane 9 (negative control). As shown in FIG. 8, the preferred combination comprised glass fiber filter pads treated with PEB (2% polysorbate 20 (TWEEN 20) in PBS) containing 2% BSA and then dried overnight at 37° C. It was further found that the preferred size of the glass fiber pad was about 7.5 mm×4 mm.

Therefore, a convenient immunostrip has the following configuration. The support member is about 89 mm×4 mm. The membrane prepared as above is about 25×4 mm and is mounted onto the support member about 5 mm from a first end of the support member. A sample pad prepared as above is mounted at the first end of the support member such that it overlaps the membrane by several millimeters. At the other end of the membrane mounted on the support member, a 25×4 mm wicking pad comprising a cellulosic material is mounted such that it overlaps the membrane by one or two millimeters. Preferably, to protect the surface of the membrane, the immunostrip is covered with a transparent polymer film except for one or two millimeters of the sample pad.

The effect of various detergents on the flow rate and signal strength was examined. The flow rate and signal strength was markedly improved when the particle blocking solution contained polysorbate 20 (TWEEN 20). The addition of about 0.075% N-Dodecyl-N,N-dimethylglycine (EMPIGEN BB, Calbiochem-Novabiochem, San Diego, Calif.) to the sample blocking solution appeared to further enhance the flow rate and signal strength. It was also found that providing the colored colored polystyrene latex particles at a concentration of about 0.10 to 0.15% in water was preferred when the above sample blocking solution was used. When using a dropper bottle to dispense the colored polystyrene latex particles in water, one drop had a volume of about 30 to 40 μL which appeared to be adequate.

Because the sample blocking solution is added to the mixture of sample and colored polystyrene latex particles, it was found to be convenient to prepare the particle blocking solution as a 2×PEB solution (2× phosphate buffered saline containing 4% polysorbate 20 (TWEEN 20)) containing 4% BSA and 0.075% EMPIGEN BB. The 2× concentrated particle blocking solution also compensates for any accidental addition of excess colored polystyrene latex particles to the sample. The volume of sample mixed with the colored polystyrene latex particles appeared to have little effect on signal strength. At a sample volume of 50 μL there appeared to be a slight, but insignificant loss of signal. Thus, the sample volume can range from at least between about 3 and 50 μL.

EXAMPLE 4

Two approaches were evaluated for providing a reference zone to the membrane of the immunostrip: a pH indicator in the reference zone which changes color when contacted by the sample solution as it flows through the membrane and an immobilized control antibody which selectively binds a control antigen bound or adsorbed to colored polystyrene latex particles.

Figure 9A:
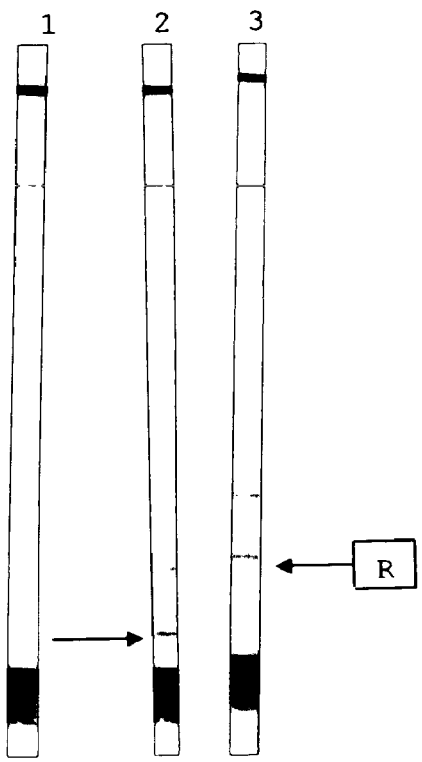
FIG. 9a shows the results of the immunoassay disclosed herein wherein the immunoassay included a control comprising 0.77 µm colored polystyrene latex particles bound to mouse IgG and the immunostrip included a reference zone which had goat anti-mouse IgG immobilized thereat. Lane 1 shows an immunostrip undeveloped. Lane 2 shows an immunostrip, which had monoclonal antibody specific for Rs EPS immobilized in the detection zone and goat anti-mouse IgG immobilized in the reference zone, and which had been immersed in a sample solution containing particles bound to Rs EPS and particles bound to mouse IgG. Lane 3 shows an immunostrip, which had monoclonal antibody specific for Rs EPS immobilized in the detection zone and goat anti-mouse IgG immobilized in the reference zone, and which had been immersed in a negative control sample containing particles bound to mouse IgG. Arrows point out EPS-bound particles captured in detection zone.
Figure 9B:
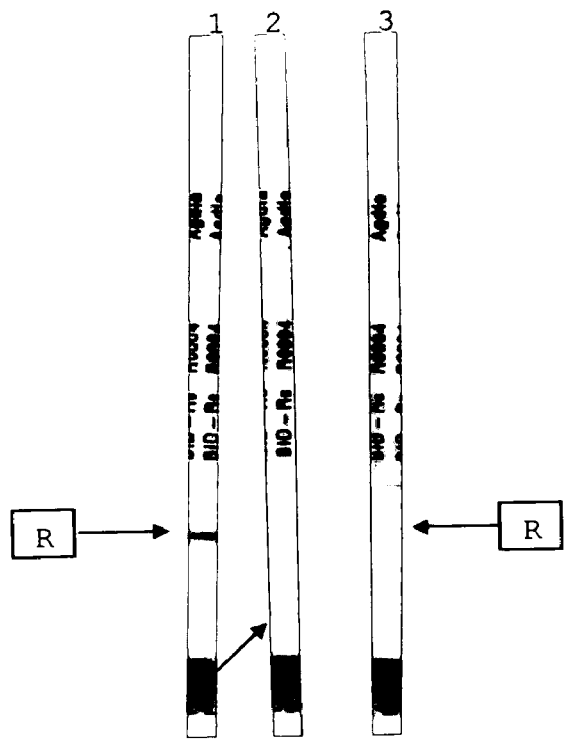
FIG. 9b shows the results of the immunoassay disclosed herein wherein the control comprised the pH indicator Bromocresol green immobilized in the reference zone. Lane 1 shows an immunostrip undeveloped. Lane 2 shows an immunostrip, which had monoclonal antibody specific for Rs EPS immobilized in the detection zone and pH indicator immobilized in the reference zone, and which had been immersed in a sample solution containing particles bound to Rs EPS. Lane 3 shows an immunostrip, which had monoclonal antibody specific for Rs EPS immobilized in the detection zone and a pH indicator immobilized in the reference zone, and which had been immersed in a negative control sample. Arrow points out EPS-bound particles captured in detection zone. Arrows labeled with "R" point out the reference zone.

Various pH indicators such as curcumin (pH 7.4-8.6), o-creslophthalein (pH 8.2-9.8), phenolphthalein (pH 8.2-10.0), alizarin (pH 5.6-8.0), bromocresol purple (pH 5.2-6.8), phenylazo benzoic acid (pH 4.8-6.6), and bromocresol green (pH 3.8-5.4) were evaluated. Control antigen/control antibody combinations such as mouse IgG as the control antigen and goat anti-mouse IgG, rabbit IgG as the control antigen and goat anti-rabbit IgG, and chicken IgY as the control antigen and goat anti-chicken IgY were evaluated. The control antigens were each adsorbed to colored polystyrene latex particles and the control antibody applied to the reference zone on the membrane such that the detection zone was between the sample pad and the reference zone. After the control and detection antibodies had been bound to the membrane, the membrane was blocked as described in Example 3. Using mouse IgG as the control antigen and goat anti-mouse IgG (FIG. 9*a*) was found to be a preferred antigen-antibody combination which also found to be preferred over the pH indicator (FIG. 9*b*).

To avoid an additional step in the immunoassay, the mouse IgG bound colored polystyrene particles were added to the 2× sample blocking solution at a concentration preferably of about 0.015%. The preferred concentration of goat anti-mouse IgG for application to the reference zone was found to be about 0.8 mg/mL.

In light of the above, the method of the immunoassay is preferably as follows. A tissue sample is removed from the plant, suspended in TBSE buffer containing 2 mM Tris-HCl, pH 9.2, 2% NaCl, and 0.01% EDTA and boiled for 5 minutes. Afterwards, a 3 to 50 µL aliquot of the boiled suspension is added to a tube containing 1 drop (30 to 50 µL) of a 0.15% solution of colored polystyrene latex particles in water. After about one minute at room temperature, one drop of 2× particle blocking solution containing 0.015% of colored polystyrene latex particles bound to control antigen (preferably, mouse IgG) is added and the mixture incubated for one minute at room temperature.

Next, the sample pad of an immunostrip prepared as described previously in Example 3 and comprising antibody against the EPS being assayed for immobilized in the detection zone and antibody against the control antigen (preferably, goat anti-mouse IgG) immobilized in the reference zone is inserted into the mixture. In general, after 10 minutes, a sufficient amount of the control antigen-colored polystyrene latex particles had flowed to the reference zone to be captured by the control antibody thereat to produce a detectable signal. Thus, any colored polystyrene latex particles bound to EPS would have been captured by the antibody in the detection zone and a detectable signal would have been visible. The sensitivity of the immunostrip assay was sufficient to detect EPS from at least between about $10^3$ to $10^4$ bacteria in a sample.

EXAMPLE 5

This example illustrates an embodiment of the present invention which uses cetyltrimethylammonium bromide (CTAB) and not boiling to extract EPS from a sample. This embodiment simplifies the extraction of EPS and because the embodiment does not rely on boiling the sample to extract the EPS, the embodiment does not require a heating means for preparing the sample which renders the immunoassay particularly useful for field use. This embodiment also preserves the viability of at least some of the bacteria in the sample during the extraction process. Thus, after the EPS has been extracted from the bacteria and an aliquot removed for immunostrip analysis, the remaining bacteria can be cultivated for further analysis.

In this embodiment, a plant tissue sample is cut into pieces or ground and added to 0.5 mL of a solution containing 0.5% CTAB and 2% NaCl in 2 mM Tris HCl, pH about 9.2. The bacteria ooze from the cut tissue and the CTAB in the presence of the high salt causes the EPS to be stripped from the bacterial envelope, aggregate, and form a precipitate. In general, one to two minutes at room temperature is sufficient to extract sufficient EPS for an immunoassay.

Next, a 3 to 50 µL aliquot of the extract mixture is added to a tube containing 1 drop (30 to 50 µL) of a 0.10 to 0.15% solution of colored polystyrene latex particles in water. After about one minute at room temperature, one drop (30 to 50 µL) of 2× particle blocking solution containing a 0.010 to 0.015% of control antigen (mouse IgG) bound to colored polystyrene latex particles is added and the mixture incubated for one minute at room temperature.

Next, the sample pad of an immunostrip prepared as described previously in Example 3 comprising antibody against the EPS being assayed for immobilized in the detection zone and antibody against the control antigen (goat anti-mouse IgG) immobilized in the reference zone is inserted into the mixture. In general, after 10 minutes, a sufficient amount of the control antigen-colored polystyrene latex particles has flowed to the reference zone to be captured by the control antibody thereat to produce a detectable signal. Thus, any colored polystyrene latex particles bound to EPS will have been captured by the antibody in the detection zone and a detectable signal will be visible.

Figure 10:
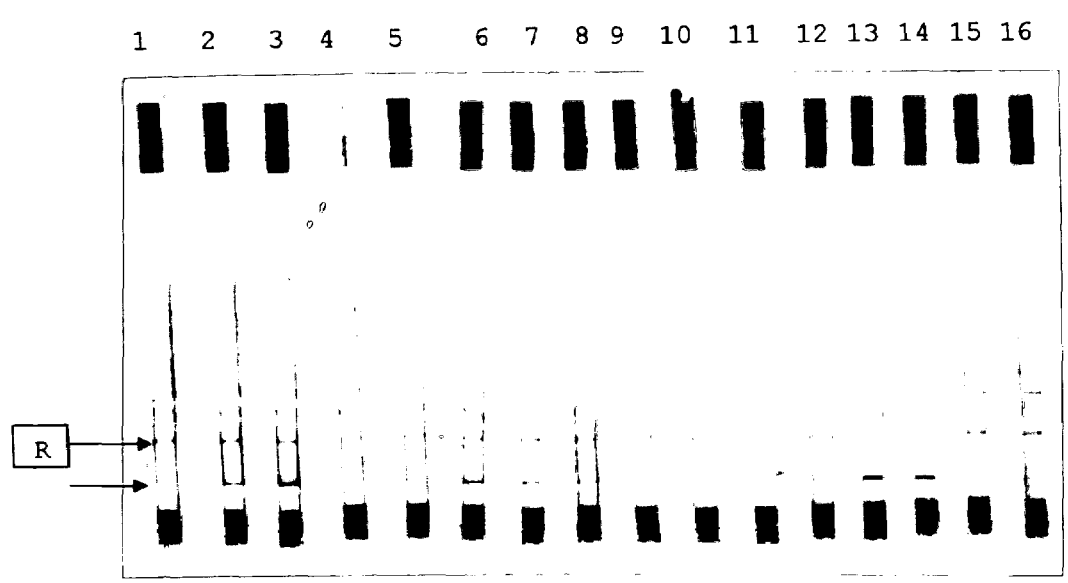
FIG. 10 shows the results of the immunoassay disclosed herein for detecting Rs EPS wherein the EPS had been extracted from infected plant tissue with CTAB. The immunostrips comprised anti-Rs antibody immobilized at the detection zone and goat anti-mouse IgG immobilized at the reference zone. Lanes 2, 3, 6, 7, 8, 12, 13, and 14 are results using extracts prepared from infected plant tissue. Lanes 1, 4, 5, 9, 10, 11, 15, and 16 are results of negative controls using extracts prepared from uninfected plant tissue. Arrow points out EPS-bound particles captured in detection zone. Arrows labeled with "R" point out control particles captured in the reference zone.

FIG. 10 shows the results for detecting EPS from a 50 mg plant tissue infected with Rs using the above CTAB extraction method.

EXAMPLE 6

The method of Example 5 was also used to detect EPS produced by *Clavibacter michiganensis* subsp. *michiganensis* (Cmm) using immunostrips in which a monoclonal antibody specific for the EPS produced by the Cmm had been immobilized at the detection zone. The immunostrips did not include a reference zone and the particle blocking solution did not contain control particles.

Figure 11A:
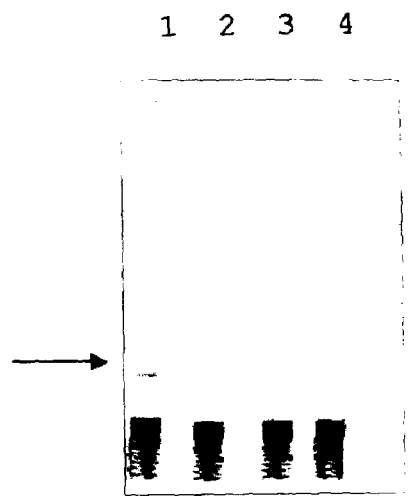
FIG. 11a shows the results of the immunoassay disclosed herein for detecting *Clavibacter michiganensis* subsp. *michiganensis* (Cmm) EPS wherein extract containing Cmm EPS is at various dilutions in extraction buffer and a monoclonal antibody specific for detecting Cmm EPS had been immobilized in the detection zone. Lane 1, neat extract; lane 2, extract diluted 1:2; lane 3, extract diluted 1:4; and, lane 4, extract diluted 1:8. Arrow points out EPS-bound particles captured in detection zone.
Figure 11B:
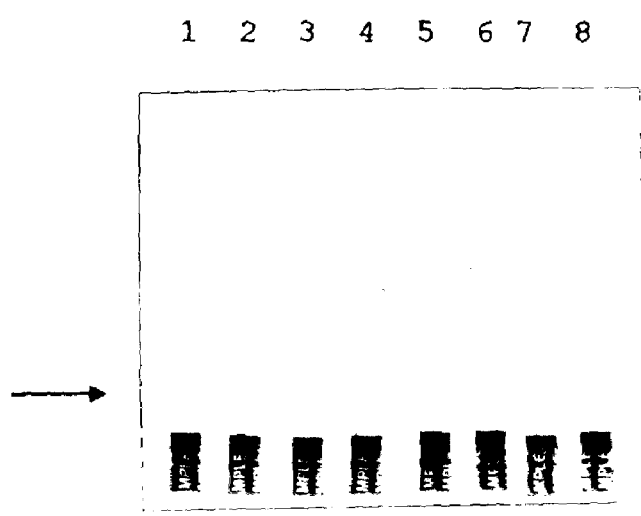
FIG. 11b shows the results of the immunoassay disclosed herein for detecting Cmm EPS wherein extract containing Cmm EPS is at various dilutions in extract prepared from non-infected tomato leaf and a monoclonal antibody specific for detecting Cmm EPS had been immobilized in the detection zone. Lane 1, neat extract; lane 2, extract diluted 1:2; lane 3, extract diluted 1:4; lane 4, extract diluted 1:8; lane 5, extract diluted 1:16; lane 6, extract diluted 1:32; and, lane 7, extract diluted 1:64. Lane 8 is a negative control. Arrow points out EPS-bound particles captured in detection zone.

The method was performed as in Example 5 using samples in which the immunostrip was immersed in Cmm EPS extracted from an infected tomato leaf sample either neat or diluted 1:2, 1:4, or 1:8 in extraction buffer or diluted 1:2, 1:4, 1:8, 1:16, 1:32, or 1:64 in extract prepared from a non-infected (healthy) tomato leaf sample. As shown in FIGS. 11a and 11b, the immunoassay was able to detect Cmm EPS at all the tested dilutions.

The immunostrips were also tested for specificity for Cmm by inserting the sample pads of immunostrips for detecting Cmm EPS into extracts prepared from a variety of uninfected plant tissues and bacteria species.

Extracts were prepared from the tissue of aloe, asparagus, banana, bean, beet root, blueberry, canola, carnation, c. quinae, corn leaf, cotton, cucumber, cymbidium, dianthus, eggplant, garlic, geranium, grape, hosta, hydrangia, kalanchoa, lily, nandina, and onion. Each extract was incubated with the colored polystyrene latex particles according to the method for detecting Cmm and then, for each extract, the sample pad of an immunostrip for detecting Cmm EPS was inserted into the extract for about 10 minutes. None of the extracts produced any compound which was detectable in the immunoassay.

Extracts were prepared with each of the following bacteria: *Acidovorax avenae* subsp. *citrulli* (Aae), *Curtobacterium flaccumfaciens* pv *poinsettiae*, *Clavibacter michiganensis* subsp. *insidiosus* (Cmi), *Clavibacter michiganensis* subsp. *michiganensis* (Cmm), *Clavibacter michiganensis* subsp. *nebraskensis* (Cmn), *Clavibacter poinsettiae*, *Clavibacter michiganensis* subsp. *sepedonicus* (Cms), *Clavibacter michiganensis* subsp. *tessellarius* (Cmt), *Erwinia carotovora* subsp. *atroseptica* (Eca), *Erwinia carotovora* subsp. *carotovora* (Ecc), *Erwinia carotovora* subsp. *chrysanthemi* (Echr), *Erwinia herbicola*, *Erwinia stewartii*, *Pseudomonas avenae*, *Pseudomonas fuscovaginae*, *Pseudomonas glumae*, *Pseudomonas syringae* pv *phaseolicola*, *Pseudomonas syringae* pv *glycincae*, *Pseudomonas syringae* pv *tomato*, *Ralstonia solanacearum*, *Xanthomonas albilineans*, *Xanthomonas campestris* pv. *armoraciae*, *Xanthomonas campestris* pv. *begoniae*, *Xanthomonas campestris* pv. *campestris*, *Xanthomonas campestris* pv. *citri*, *Xanthomonas campestris* pv. *dieffenbachiae*, *Xanthomonas campestris* pv. *oryzae*, *Xanthomonas campestris* pv. *pelargonii*, *Xanthomonas campestris* pv. *phaseoli*, *Xanthomonas campestris* pv *transluciens*, *Xanthomonas campestris* pv *vesicatora*, *Xanthomonas campestris* pv *zinnea*, *Xanthomonas maltophilia*, *Acinetobacter calcoacaticus*, *Bacillus cerelis*, *Bacillus subtilis*, *Escherichia coli*, *P. aeringinosa*, *Pseudomonas fluorescens*, *Pseudomonas putida*, *Serritia marcesens*, *Streptococcus aurelius*, and *Streptococcus faecalis*. Each extract was incubated with the colored polystyrene latex particles according to the method for detecting Cmm and then, for each extract, the sample pad of an immunostrip for detecting Cmm EPS was inserted into the extract for about 10 minutes. None of the bacterial extracts contained EPS or LPS which was cross-reactive and detectable in the immunoassay except for the related *Clavibacter michiganensis* subspecies Cmi, Cmn, and Cms. Thus, the above Cmm immunoassay is useful not only for assaying tomato tissue for the presence of Cmm but also alfalfa tissue for Cmi, corn tissue for Cmn, and potato tissue for Cms. Interestingly, the anti-Cmm EPS monoclonal antibody was unable to detect the EPS of the related Cmt which causes bacterial mosaic of wheat.

The above results demonstrate that the method of the present invention is specific for detecting EPS or LPS of a particular microorganism as long as the detection zone comprises an antibody which is specific for the EPS or LPS produced by the microorganism. The specificity of the immunoassay is dependent on the specificity of the antibody. In light of the above results with Cmi, Cms, and Cmn, single immunoassays can be provided which have the ability to detect the EPS or LPS of several closely related bacterial species each of which infects a different host.

EXAMPLE 7

In this example, the immunoassay was used to detect particular potyviruses in plant tissue. Immunoassays for detecting the following potyviruses were performed: Bean Common Mosaic Virus (BCMV), Dasheen Mosaic Virus (DsMV), Johnsongrass Mosaic virus (JgMV), Lettuce Mosaic Virus (LMV), Maize Dwarf Mosaic Virus (MDMV), Onion Yellow Dwarf Virus (OYDV), Pepino Mosaic Virus (PepMV), Pepper Mottle Virus (PepMoV), Plum Pox Virus (PPV), Papaya Ringspot Virus (PRSV), Pea Seed-Borne Mosaic Virus (PSbMV), Potato Virus A (PVA), Potato Virus Y (PVY), Potato Virus Y necrotic strain (PVY-n), Soybean Mosaic Virus (SMV), Sugarcane Mosaic Virus (SCMV), Tobacco Etch Virus (TEV), Tobacco Vein Mottling Virus (TVMV), Watermelon Mosaic Virus 2 (WMV2), and Zucchini Yellow Mosaic Virus (ZYMV). The immunoassay for each plant tissue infected with one of the above viruses was performed as follows.

Plant tissue was added to a carbonate-bicarbonate buffer pH 9.0 at a ratio of about 1 gram to 5 grams of buffer, 1 gram to 10 grams of buffer, 1 gram to 20 grams of buffer, or 1 gram to 50 grams of the buffer and ground at room temperature for several minutes.

Next, a 25 to 50 µL aliquot of the mixture was added to a tube containing 1 drop (30 to 50 µL) of a 0.10 to 0.15% solution of colored polystyrene latex particles in water. After about one minute at room temperature, one drop (30 to 50 µL) of 2× particle blocking solution containing a 0.010 to 0.015% of control antigen (mouse IgG) bound to colored polystyrene latex particles was added and the mixture incubated for one minute at room temperature.

Figure 12A:
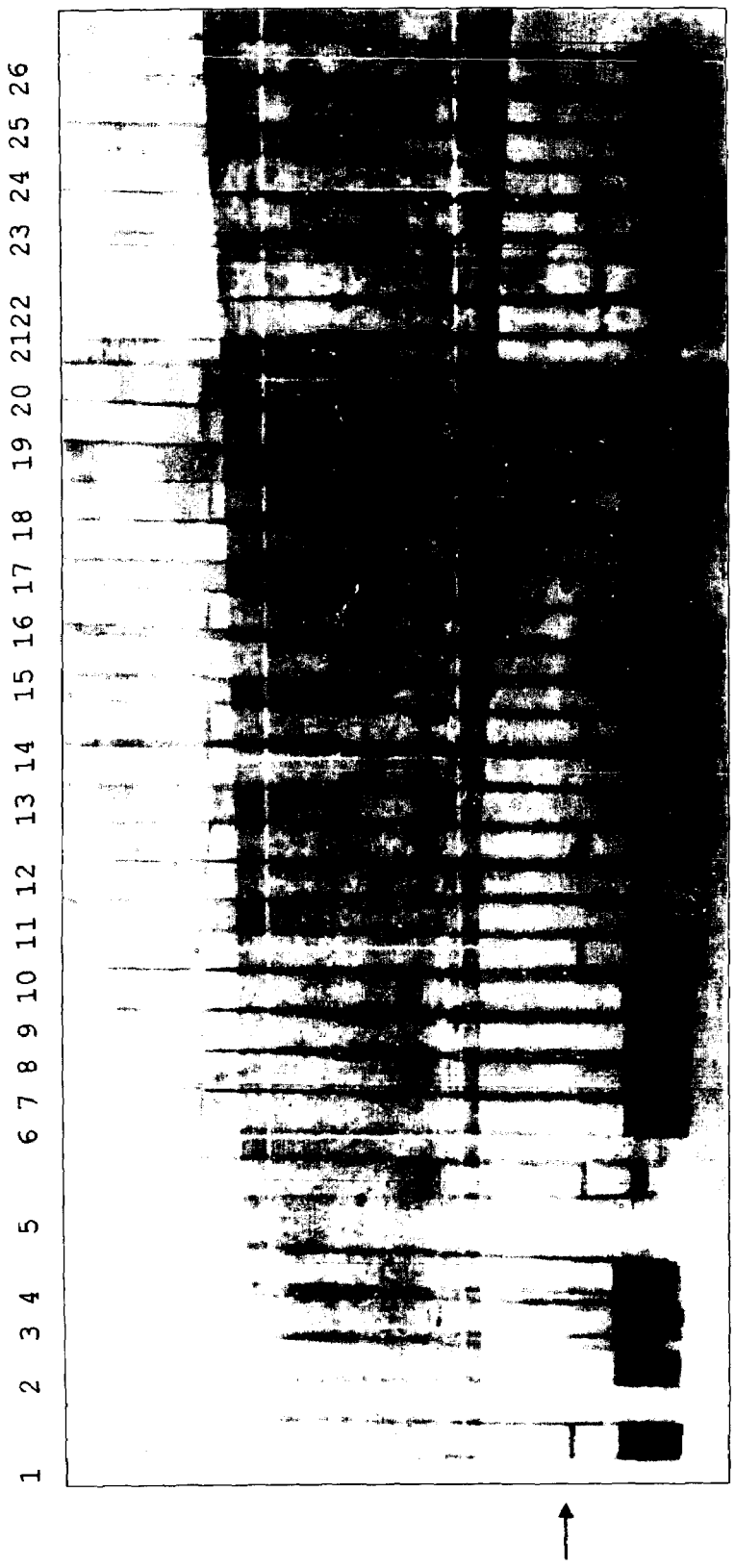
FIG. 12a shows the results of the immunoassay disclosed herein wherein a monoclonal antibody specific for SCMV, BCMV, MDMV, JgMV, LMV, PepMV, PPV, PRSV, PsbMV, PVA, PVY, SMV, or WMV2 had been immobilized in the detection zone of the immunostrips. The extracts for each of the potyviruses had been diluted with extraction solution for the immunoassay as follows. Lane 1, SCMV diluted 1:20; lane 2, BCMV diluted 1:5; lane 3, BCMV diluted 1:10; lane 4, BCMV diluted 1:50; lane 5, MDMV diluted 1:10; lane 6, JgMV diluted 1:5; lane 7, JgMV diluted 1:10, lane 8, JgMV diluted 1:50; lane 9, LMV diluted 1:5; lane 10, LMV diluted 1:10; lane 11, PepMV diluted 1:5; lane 12, PepMV diluted 1:10; lane 13, PPV diluted 1:5; lane 14, PPV diluted 1:10; lane 15, PRSV diluted 1:5; lane 16, PRSV diluted 1:10; lane 17, PsbMV diluted 1:5; lane 18, PsbMV diluted 1:10; lane 19, PVA diluted 1:5; lane 20, PVA diluted 1:10; lane 21, PVY diluted 1:5; lane 22, PVY diluted 1:10; lane 23, SMV diluted 1:5; lane 24, SMV diluted 1:10; lane 25, WMV2 diluted 1:5; and, lane 10, WMV2 diluted 1:10. Arrow points out virus-bound particles captured in detection zone.
Figure 12B:
FIG. 12b shows the results of the immunoassay disclosed herein wherein a monoclonal antibody specific for BCMV (lane 1), DSMV (lane 2), LMV (lane 3), JgMV (lane 4), MDMV (lane 5), OYDV (lane 6), PepMV (lane 7), PPV (lane 8), PRSV (lane 9), PsbMV (lane 10), PVA (lane 11), PVY (lane 12), PVY-n (lane 13), SMV (lane 14), TEV (lane 15), TVMV (lane 16), WMV2 (lane 17), or ZYMV (lane 18) had been immobilized in the detection zone of the immunostrips. The extracts for each of the potyviruses had been diluted 1:10 with extraction solution for the immunoassay. Arrow points out virus-bound particles captured in detection zone.
Figure 12B:

Next, the sample pad of an immunostrip prepared as described previously in Example 3 comprising antibody against the coat protein of the particular potyvirus being assayed for immobilized in the detection zone but without a reference zone was inserted into the mixture for about 10 minutes. The results shown in FIGS. 12*a* and 12*b* demonstrate that the immunoassay of the present invention can be used to detect potyviruses from extracts prepared from infected plant tissue. The results also show that the other components of the extract did not appear to interfere with the sensitivity of the immunoassay.

EXAMPLE 8

This example shows that the immunoassay of the present invention is able to detect various concentrations of potyvirus.

Potyvirus was suspended in a carbonate-bicarbonate buffer pH 9.0 at 0.02 mg/mL, 0.01 mg/mL, and 0.005 mg/mL. A control consisted of buffer without virus.

Next, a 25 to 50 µL aliquot of the mixture was added to a tube containing 1 drop (30 to 50 µL) of a 0.10 to 0.15% solution of colored polystyrene latex particles in water. After about ten minutes at room temperature, one drop (30 to 50 µL) of 2× particle blocking solution containing a 0.010 to 0.015% of control antigen (mouse IgG) bound to colored polystyrene latex particles was added and the mixture incubated for one minute at room temperature.

Figure 13:
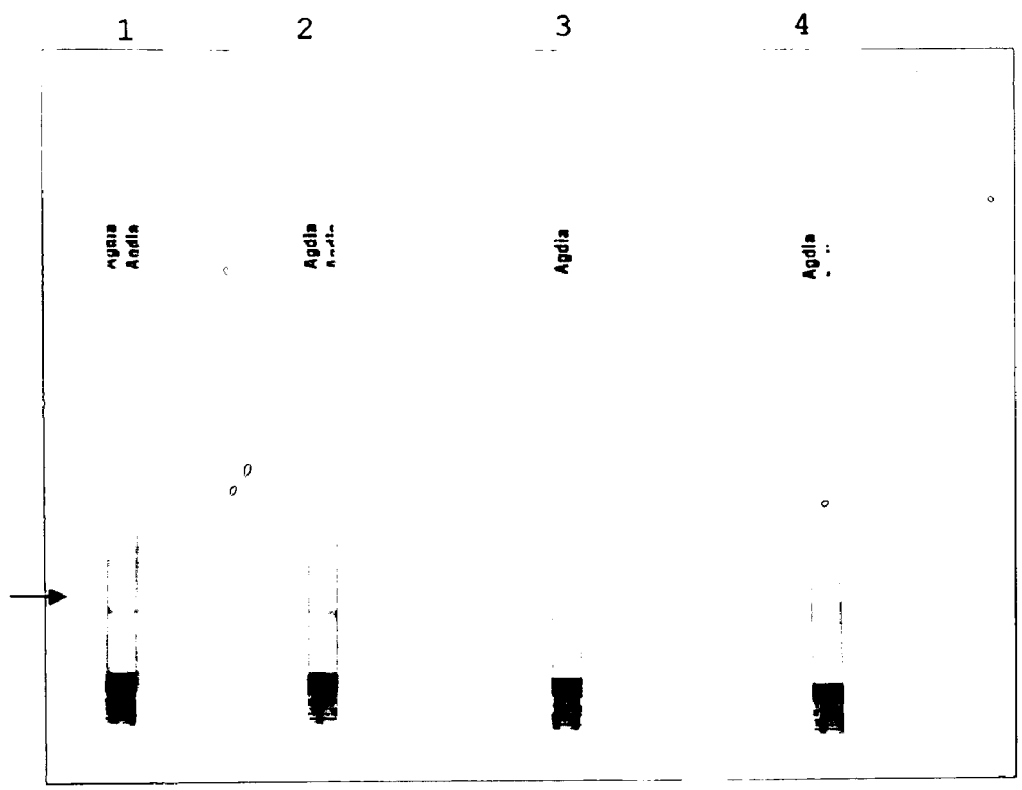
FIG. 13 shows the results of the immunoassay disclosed herein for detecting potyvirus. The immunostrips had monoclonal antibody specific for the potyvirus coat protein immobilized in the detection zone and the samples tested contained 0.02 mg/mL (lane 1), 0.01 mg/mL (lane 2), and 0.005 mg/mL (lane 3) of the virus. Lane 4 is a negative control. Arrow points out virus-bound particles captured in detection zone.

Next, the sample pad of an immunostrip prepared as described previously in Example 3 comprising antibody against the potyvirus coat protein immobilized in the detection zone but without a reference zone was inserted into the mixture for about 10 minutes. The results shown in FIG. 13 demonstrate that the immunoassay of the present invention can detect potyvirus in an aliquot from a sample in which the virus is at a concentration as low as 0.005 mg/mL.

EXAMPLE 9

In this example, the immunoassay of the present invention was used to detect various concentrations of the carmovirus calibrachoa mottle virus (CbMV).

CbMV was added to a carbonate-bicarbonate buffer pH 9.0 at 0.02 mg/mL, 0.01 mg/mL, and 0.005 mg/mL. A control consisted of buffer without the virus.

Next, a 25 to 50 µL aliquot of the mixture was added to a tube containing 1 drop (30 to 50 µL) of a 0.10 to 0.15% solution of colored polystyrene latex particles in water. After about ten minutes at room temperature, one drop (30 to 50 µL) of 2× particle blocking solution containing a 0.010 to 0.015% of control antigen (mouse IgG) bound to colored polystyrene latex particles was added and the mixture incubated for one minute at room temperature.

Figure 14:
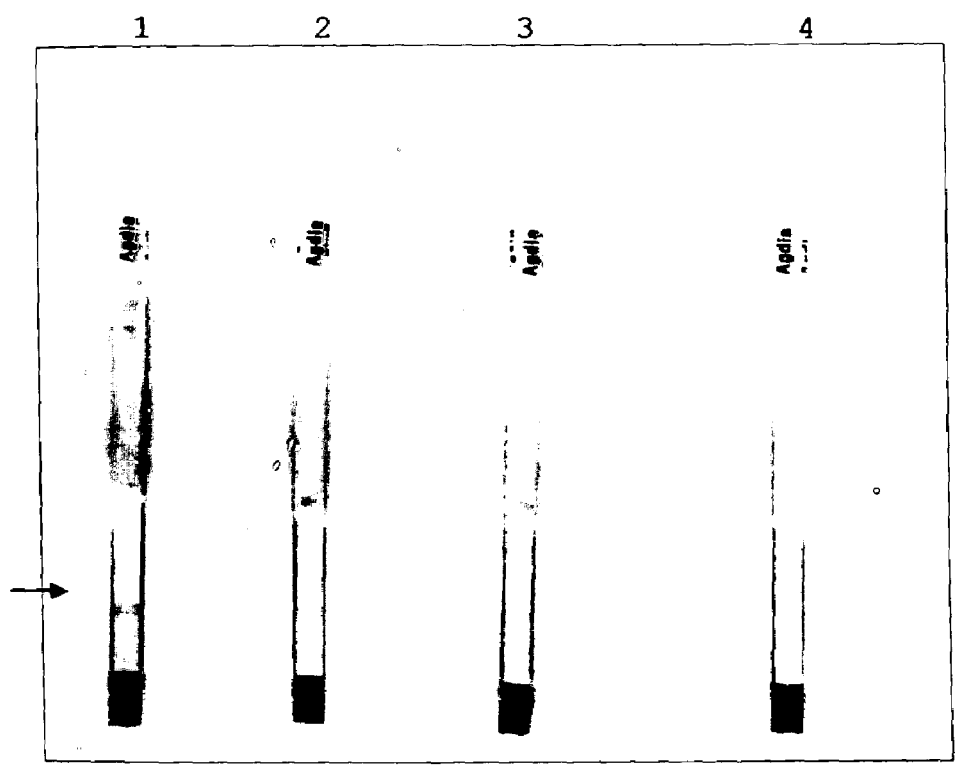
FIG. 14 shows the results of the immunoassay disclosed herein for detecting CbMV. The immunostrips had monoclonal antibody specific for the CbMV coat protein immobilized in the detection zone and the samples tested contained 0.02 mg/mL (lane 1), 0.01 mg/mL (lane 2), and 0.005 mg/mL (lane 3) of the virus. Lane 4 is a negative control. Arrow points out virus-bound particles captured in detection zone.

Next, the sample pad of an immunostrip prepared as described previously in Example 3 comprising antibody against the CbMV immobilized in the detection zone but without a reference zone was inserted into the mixture for about 10 minutes. The results shown in FIG. 14 demonstrate that the immunoassay of the present invention can detect calibrachoa virus in an aliquot from a sample in which the virus is at a concentration as low as 0.005 mg/mL of infected plant tissue. The results also show that the other components of the extract did not appear to interfere with the sensitivity of the immunoassay.

EXAMPLE 10

An immunoassay as described in Example 5 was performed which shows that the immunoassay can readily detect EPS from low concentrations of bacteria in a sample.

Cmm was added to carbonate-bicarbonate buffer pH 9.0 and samples containing 30,000 bacteria/mL, 7,500 bacteria/mL, and 1,875 bacteria/mL were produced. The EPS was extracted with CTAB as described previously and then 10 µL of extract from each dilution of bacteria was added to a 0.15% suspension of colored polystyrene latex particles in water.

Figure 15:
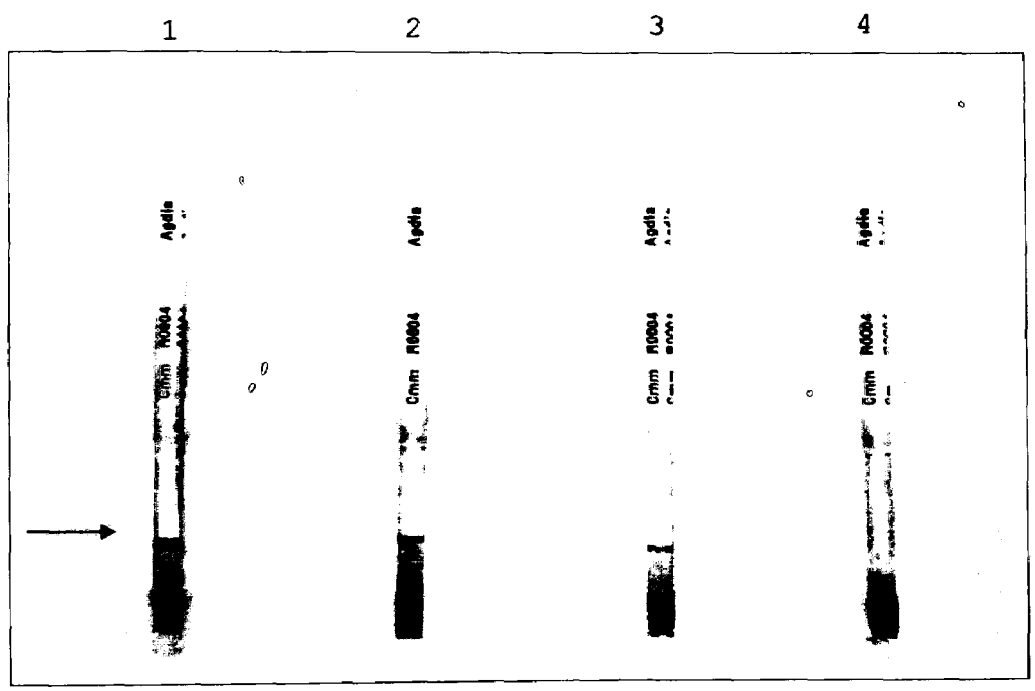
FIG. 15 shows the results of the immunoassay disclosed herein for detecting Cmm EPS. The immunostrips had monoclonal antibody specific for Cmm EPS immobilized in the detection zone and the samples contained 30,000 bacteria/mL (lane 1), 7,500 bacteria/mL (lane 2), and 1,875 bacteria/mL (lane 3). Lane 4 is a negative control. Arrow points out EPS-bound particles captured in detection zone.

After about a minute, one drop of 2× particle blocking solution without control particles was added and the sample pads of immunostrips for detecting Cmm prepared as described previously were immersed in the samples. FIG. 15 shows that the immunoassay can detect EPS in a 10 µL aliquot from samples containing as little as 1,875 bacteria/mL.

EXAMPLE 11

In this example, the immunoassay of the present invention was used to detect antibodies from various animal species using immunostrips comprising antibody specific for the antibody to be detected immobilized in the detection zone.

Chicken IgY was added to carbonate-bicarbonate buffer pH 9.0 to produce samples containing 0.02 mg/mL, 0.01 mg/mL, and 0.005 mg/mL of the IgY. Rabbit IgG was added to carbonate-bicarbonate buffer pH 9.0 to produce samples containing 0.02 mg/mL, 0.01 mg/mL, and 0.005 mg/mL of the IgG. Mouse IgM was added to carbonate-bicarbonate buffer pH 9.0 to produce samples containing 0.02 mg/mL and 0.01 mg/mL of the IgM. For each of the above samples, an aliquot was removed and added to a 0.015% suspension of colored polystyrene latex particles in water. After 5 minutes the particles were blocked with the addition of one drop of 2× particle blocking solution and the samples assayed as follows. For each antibody species, a negative control was included.

For each chicken IgY sample, the sample pad of an immunostrip prepared as previously described to comprise goat anti-chicken IgY immobilized in the detection zone was immersed in the sample. For each rabbit IgG sample, the sample pad of an immunostrip prepared as previously described to comprise goat anti-rabbit IgG immobilized in the detection zone was immersed in the sample. For each mouse IgM sample, the sample pad of an immunostrip prepared as previously described to comprise goat anti-mouse IgM immobilized in the detection zone was immersed in the sample.

Figure 16:
FIG. 16 shows the results of the immunoassay disclosed herein for detecting chicken IgY. The immunostrips had goat anti-chicken IgY antibody immobilized in the detection zone and the samples contained 0.02 mg/mL (lane 1), 0.01 mg/mL (lane 2), and 0.005 mg/mL (lane 3) of the IgY. Lane 4 is a negative control. Arrow points out IgY-bound particles captured in detection zone.
Figure 17:
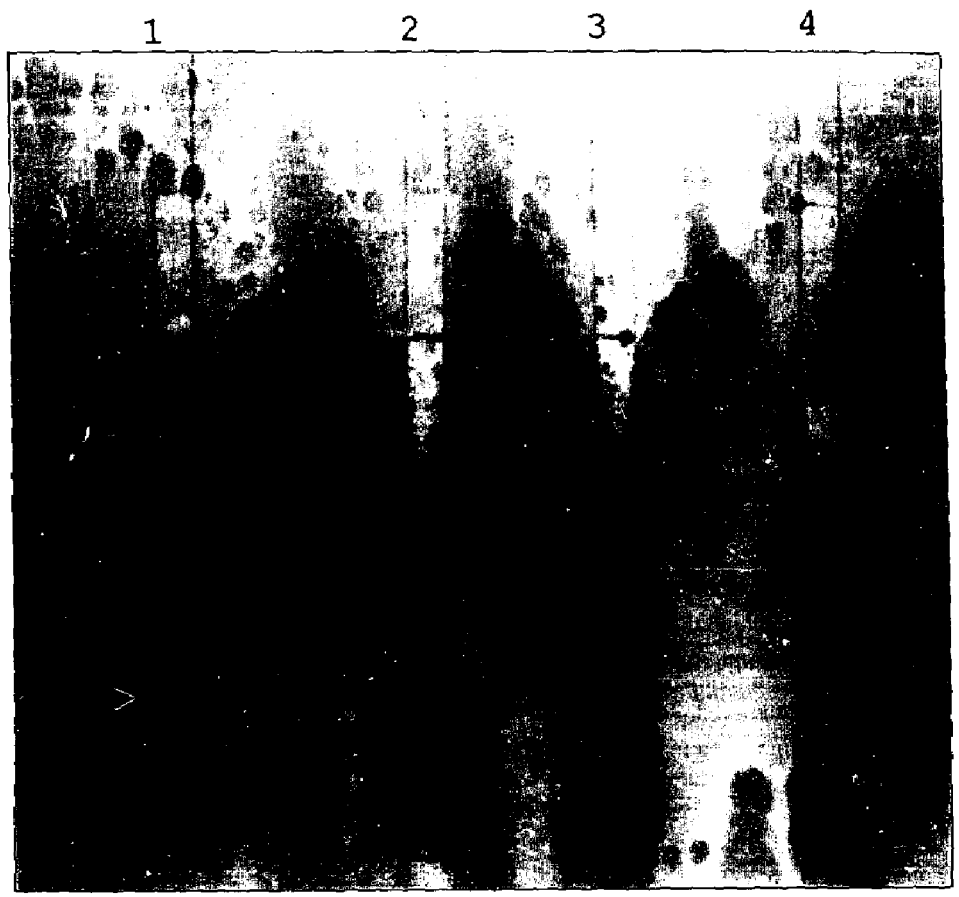
FIG. 17 shows the results of the immunoassay disclosed herein for detecting rabbit IgG. The immunostrips had goat anti-rabbit IgG antibody immobilized in the detection zone and the samples contained 0.02 mg/mL (lane 1), 0.01 mg/mL (lane 2), and 0.005 mg/mL (lane 3) of the IgG. Lane 4 is a negative control. Arrow points out IgG-bound particles captured in detection zone.
Figure 18:
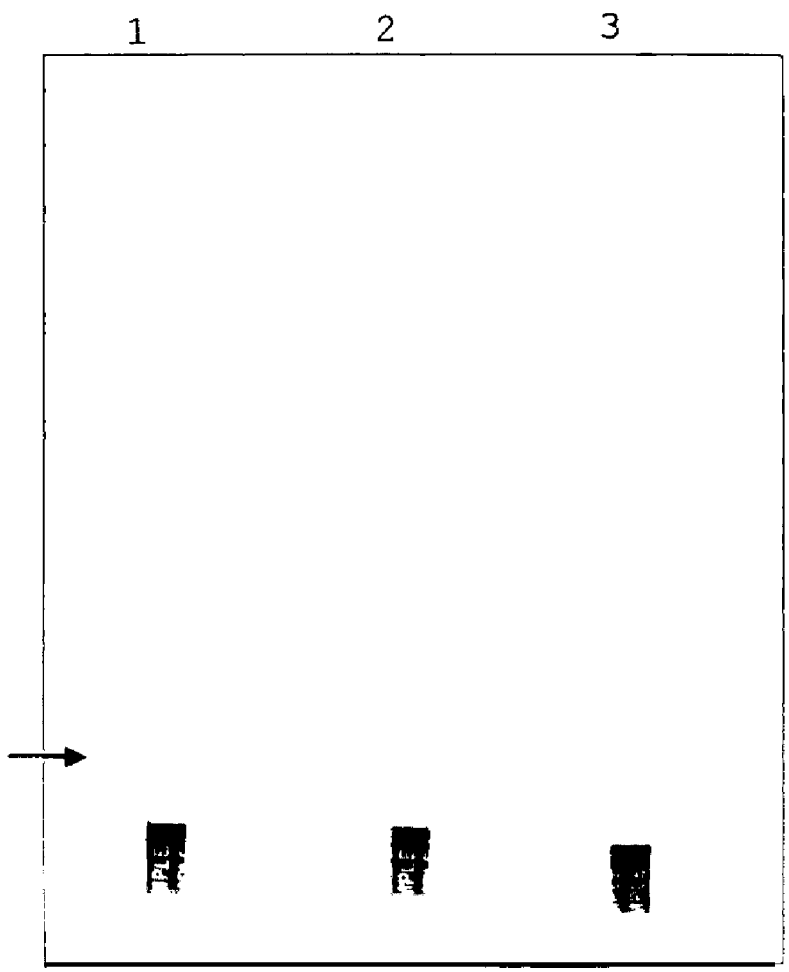
FIG. 18 shows the results of the immunoassay disclosed herein for detecting mouse IgM. The immunostrips had goat anti-mouse IgM antibody immobilized in the detection zone and the samples contained 0.02 mg/mL (lane 1) and 0.01 mg/mL (lane 2) of the IgM. Lane 3 is a negative control. Arrow points out IgM-bound particles captured in detection zone.

For each antibody species, the immunostrips were able to detect each species of antibody at each of the concentrations tested. The results for detecting chicken IgY are shown in FIG. 16, the results for detecting rabbit IgG are shown in FIG. 17, and the results for detecting mouse IgM are shown in FIG. 18. The results further demonstrate that the above antibody species are useful as controls.

EXAMPLE 12

In this example, the immunoassay of the present invention is used to screen a monoclonal antibody library prepared against the recombinant CP4 protein, which in transgenic plants harboring the gene encoding the CP4, confers resistance to ROUNDUP READY herbicide.

Methods for producing monoclonal antibody libraries are well known in the art. For example, a monoclonal antibody library can be prepared by immunizing BALB/c mice with an initial injection of about 1 µg CP4 per mouse mixed 1:1 with Titer max, Freund's incomplete adjuvant or Freund's complete adjuvant. After two weeks, a booster injection of about 1 µg of CP4 is injected into each mouse intravenously without adjuvant. Three days after the booster injection a fusion is performed with a mouse myeloma cell line. Mid log phase myeloma cells are harvested on the day of fusion, checked for viability, and separated from the culture medium by low-speed centrifugation. Then the cells are resuspended in serum-free Dulbecco's Modified Eagle's medium (DMEM).

The spleens are removed from the immunized mice and washed three times with serum-free DMEM and placed in a sterile Petri dish containing DMEM containing 20% fetal bovine serum, 1 mM pyruvate, 100 units penicillin, and 100 units streptomycin. The cells are released by perfusion. The cells are pelleted by low-speed centrifugation and the cell pellet is resuspended in 10 ml serum-free DMEM medium. Then 5 ml of 20% bovine fetal serum is added and the cells pelleted by low-speed centrifugation. Afterwards, the cells are resuspended in 10 ml DMEM and mixed with myeloma cells to give a ratio of 3:1. The cell mixture is pelleted by low-speed centrifugation, the supernatant fraction removed, and the pellet allowed to stand for 5 minutes. Next, over a period of 1 minute, 1 mL of 50% polyethylene glycol (PEG) in 0.01 M HEPES pH 8.1 at 37° C. is added. After 1 minute incubation at 37° C., 1 mL of DMEM is added for a period of another 1 minute, then a third addition of DMEM is added for a further period of 1 minute. Finally, 10 mL of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 µM aminopterin, and 10% hybridoma cloning factor (HAT medium). The cells are then plated into 96-well plates.

After 3, 5, and 7 days half the medium in the plates is removed and replaced with fresh HAT medium. After 11 days, the hybridoma cell supernatant is screened using immunostrips comprising anti-mouse IgG immobilized in the detection zone. The immunostrip is prepared as described in Example 4. CP4 is bound to colored polystyrene latex particles and the particles then blocked with 2× particle blocking solution.

To screen the library, 100 µL aliquots from each of the wells of the above 96-well plates is separately pipetted to a corresponding well in a 96-well plate along with 100 µL of the particles bound with CP4. After about 1 to 5 minutes at room temperature, for each well, the sample pad of an immunostrip is immersed in the well. The CP4-bound particles bind to mouse anti-CP4 IgG, if present. The complex then travels chromatographically through the membrane of the immunostrip and is captured by the anti-mouse antibody in the detection zone which is detectable as a colored band in the detection zone.

The advantages of this screening method over prior art screening methods are that the screening can be done rapidly, antibodies with high affinity (binds antigen at a faster rate) can be preferentially selected by allowing less incubation time with the antigen-bound particles, and antibodies which perform in an immunostrip format are preferentially selected. The above method can be used for screening monoclonal and phage display libraries for clones expressing antibodies or recombinant antibodies against EPS, LPS, and particular viruses such as the viruses disclosed herein.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method for detecting the presence of an infection in a plant caused by a virus selected from the group consisting of potyviridae and tobamoviridae, which comprises:
    (a) providing a detection apparatus which includes mounted on a support member an elongated membrane having a first end and a second end wherein in lateral contact with the first end of the membrane is a sample pad for receiving a liquid sample and in lateral contact with the second end of the membrane is a wicking pad which allows the liquid sample to flow through the membrane from the sample pad to the wicking pad and wherein the membrane further comprises at least one detection zone laterally spaced from the sample pad in which is immobilized an antibody which is specific for a protein of the virus end a reference zone laterally spaced between the detection zone and the wicking pad in which is immobilized a control antibody;

(b) mixing a material from the plant with an extraction solution for a time sufficient to produce a mixture including the protein of the virus;

(c) mixing an aliquot of the mixture from step (b) with naked, unmodified, visible polystyrene latex particles which bind to the protein of the virus at room temperature for a time sufficient to bind a sufficient amount the protein of the virus to the particles to enable visualization of the particles bound to the protein and without substantial binding of other components of the mixture to the particles;

(d) mixing a particle blocking solution including a blocking agent with the mixture in step (c) at room temperature for a time sufficient to block sites on the particles not bound to the proteins of the virus; and (e) applying the mixture from step (d) to the sample pad in the detection apparatus at room temperature wherein binding of (i) the protein of the virus bound to the particles by (ii) the antibody specific for the protein of the virus that is immobilized in the detection zone indicates the presence of the infection.

2. The method of claim 1 wherein the extraction solution is a carbonate-bicarbonate buffer.

3. The method of claim 2 wherein the buffer has a pH of about 9.6.

4. The method of claim 1 wherein the particle blocking agent is bovine serum albumin.

5. The method of claim 1 wherein the particle blocking solution includes bovine serum albumin and polysorbate 20 in a buffer.

6. The method of claim 1 wherein the particle blocking solution includes bovine serum albumin, polysorbate 20, and n-dodecyl-N,N-dimethyl glycine in a buffer.

7. The method of claim 1 wherein the polystyrene latex particles have a diameter from about 0.06 μm to 1.0 μm.

8. The method of claim 1 wherein the membrane is a nitrocellulose membrane.

9. The method of claim 1 wherein the nitrocellulose membrane has a pore size from about 10 to 20 μm.

10. The method of claim 1 wherein the membrane has been treated with a membrane blocking agent.

11. The method of claim 10 wherein the membrane blocking agent is bovine serum albumin.

12. The method of claim 1 wherein the sample pad includes a polyester or glass fibers.

13. The method of claim 1 wherein the sample pad has been treated with a sample pad blocking agent.

14. The method of claim 13 wherein the sample pad blocking agent is selected from the group consisting of bovine serum albumin, non-fat dry milk, and mixtures thereof.

15. The method of claim 1 wherein the wicking pad includes a cellulosic material.

16. The method of claim 1 wherein the particle blocking solution further includes particles which have bound thereon an antigen which binds the control antibody.

17. The method of claim 1 wherein the naked, unmodified, visible polystyrene latex particles are colored and enable visualization by the human eye in visible light.

18. The method of claim 1 wherein the naked, unmodified, visible polystyrene latex particles are colored and enable visualization by the human human eye or a machine reader upon illumination with an ultraviolet light.

19. The method of claim 1 wherein the naked, unmodified, visible polystyrene latex particles are free of conjugated antibodies.

* * * * *

UNITED STATES PATENT AND TRADEMARK OFFICE
CERTIFICATE OF CORRECTION

PATENT NO. : 7,585,641 B2  Page 1 of 1
APPLICATION NO. : 10/348078
DATED : September 8, 2009
INVENTOR(S) : Bandla et al.

It is certified that error appears in the above-identified patent and that said Letters Patent is hereby corrected as shown below:

Column 40, lines 31-34, Claim 18, Claim 18 should read -The method of Claim 1 wherein the naked, unmodified, visible polystyrene latex particles are fluorescently labeled and enable visualization by the human eye or a machine reader upon illumination with an ultraviolet light.-

Signed and Sealed this

Second Day of February, 2010

David J. Kappos
*Director of the United States Patent and Trademark Office*